United States Patent [19]

Sugaya et al.

[11] Patent Number: 5,079,358
[45] Date of Patent: Jan. 7, 1992

[54] 6H-PYRAZOLO-[4,5,1-D,E]ACRIDIN-6-ONE DERIVATIVES HAVING ANIT-TUMOR ACTIVITY

[75] Inventors: Toru Sugaya, Nara; Yukiteru Mimura, Shizuoka; Yasushi Shida, Shizuoka; Yutaka Osawa, Shizuoka; Ikuo Matsukuma, Tokyo; Shiro Akinaga, Shizuoka; Makoto Morimoto, Shizuoka, all of Japan

[73] Assignee: Kyowa Hakko Kogyo Co., Ltd., Tokyo, Japan

[21] Appl. No.: 365,736

[22] Filed: Jun. 14, 1989

[30] Foreign Application Priority Data

Jun. 20, 1988 [JP] Japan ............................. 63-151677

[51] Int. Cl.$^5$ ............... C07D 471/06; C07D 231/00; C07D 221/00
[52] U.S. Cl. ........................... 544/58.6; 544/125; 544/361; 546/66
[58] Field of Search ........... 546/66; 544/125, 58.6, 544/361; 514/288, 233.2, 228.2, 253

[56] References Cited

U.S. PATENT DOCUMENTS

| | | | |
|---|---|---|---|
| 3,920,662 | 11/1975 | Troster | 546/66 |
| 4,202,897 | 5/1980 | Babington et al. | 514/288 |
| 4,556,654 | 12/1985 | Showalter et al. | 514/222 |

FOREIGN PATENT DOCUMENTS 0138302  4/1985  European Pat. Off. .............. 546/66

OTHER PUBLICATIONS

Hadley, Endocrinology [Prentice Hall, Englewood Cliffs, N.J.], 1984, p. 463.
The Merck Manual, 15th Ed. (Merck and Co., 1987, Rahway, N.J.), pp. 704–707.
Schimmelschmidt et al., Ann. Chem. 677, pp. 157–160.

*Primary Examiner*—Mukund J. Shah
*Assistant Examiner*—E. C. Ward
*Attorney, Agent, or Firm*—Fitzpatrick, Cella, Harper & Scinto

[57] ABSTRACT

Novel pyrazoloacridone compounds represented by the following formula:

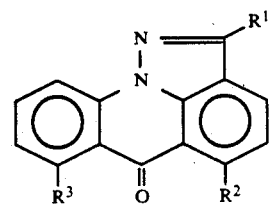

and pharmaceutically acceptable salts thereof have an excellent anti-tumor activity.

7 Claims, No Drawings

6H-PYRAZOLO-[4,5,1-D,E]ACRIDIN-6-ONE DERIVATIVES HAVING ANIT-TUMOR ACTIVITY

BACKGROUND OF THE INVENTION

The present invention relates to pyrazoloacridone derivatives having anti-tumor activity.

As a pyrazoloacridone derivative, 6H-pyrazolo[4,5,1-d,e]acridin-6-one, which is the compound of the formula (I) mentioned below wherein $R^1$, $R^2$ and $R^3$ are hydrogen atoms, is known [Ann. Chem., 677, 157 (1964)]. However, pyrazoloacridone derivatives having anti-tumor activity have not been known.

As tetracyclic heterocyclic compounds having anti-tumor activity, anthra[1,9-c,d]pyrazol-6(2H)-one derivatives wherein anthraquinone and pyrazole ring are peri-fused are disclosed in Japanese Published Unexamined Patent Application No. 51268/82 (U.S. Pat. No. 4,556,654).

SUMMARY OF THE INVENTION

The present invention provides novel pyrazoloacridone derivatives which are expected to be useful as anti-tumor agents, based on the finding that pyrazoloacridone derivatives of some kind have anti-tumor activity.

Specifically, the present invention relates to pyrazoloacridone derivatives represented by the following formula (I) and their pharmaceutically acceptable salts. [The derivatives are hereinafter referred to as Compounds (I). The same shall apply to the compounds of other formula numbers.]

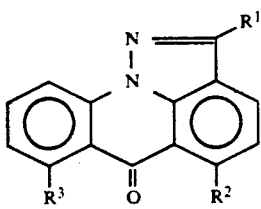

In the formula, $R^1$ represents —CH$_2$X in which X represents hydrogen —NR$^{4a}$R$^{4b}$ (wherein R$^{4a}$ and R$^{4b}$ are the same or different and each represents R$^4$, or they form a heterocyclic group together with the adjacent nitrogen atom), —OR$^4$ or —SR$^4$; R$^4$ represents hydrogen or optionally substituted lower alkyl, the substituent for the said alkyl being halogen, —NR$^{5a}$R$^{5b}$ (wherein R$^{5a}$ and R$^{5b}$ are the same or different and each represents R$^5$, or they form a heterocyclic group together with the adjacent nitrogen atom), —OR$^5$ or —SR$^5$; R$^5$ represents hydrogen or optionally substituted lower alkyl, the substituent for the said alkyl being halogen, —NR$^{6a}$R$^{6b}$ (wherein R$^{6a}$ and R$^{6b}$ are the same or different and each represents R$^6$, or they form a heterocyclic group together with the adjacent nitrogen atom), —OR$^6$ or —SR$^6$; and R$^6$ represents hydrogen or lower alkyl; or R$^1$ represents —COY in which Y represents hydrogen, —NR$^{41}$R$^{4b}$ (wherein R$^{4a}$ and R$^{4b}$ have the same meanings as defined above) or —OR$^4$ (wherein R$^4$ has the same meaning as defined above); R$^2$ represents hydrogen, halogen, nitro, —NR$^{4A}$R$^{4B}$ (wherein R$^{4A}$ and R$^{4B}$ have the same meanings as R$^{4a}$ and R$^{4b}$ mentioned above or they represent optionally halogen-substituted lower alkanoyl) or —OR$^{4c}$ (wherein R$^{4c}$ has the same meaning as R$^4$ mentioned above); and R$^3$ represents hydrogen, halogen, hydroxyl, lower alkoxyl or benzyloxy.

DETAILED DESCRIPTION OF THE INVENTION

In the definition of R$^1$, the heterocyclic group to be formed together with the adjacent nitrogen atom means a 5 to 7-membered heterocyclic group, which includes alicyclic heterocyclic groups such as pyrrolidine, piperidine, morpholine, thiomorpholine, piperazine, N-substituted piperazine, homopiperazine and N-substituted homopiperazine, and aromatic heterocyclic groups such as imidazole, oxazole and thiazole. As the substituent, lower alkyl and optionally halogen-substituted lower alkanoyl may be mentioned.

In the definitions of the groups in the formula (I), the alkyl moiety in the lower alkyl and lower alkoxyl groups is a straight-chain or branched alkyl group having 1 to 6 carbon atoms such as methyl, ethyl, n-propyl, isopropyl, n-butyl, isobutyl, sec-butyl, tert-butyl, n-pentyl, isopentyl and n-hexyl. The halogen includes fluorine, chlorine, bromine and iodine. The lower alkanoyl group is a straight-chain or branched lower alkanoyl group having 1 to 6 carbon 1, propionyl, n-butyryl, isobutyryl and n-pentanoyl, and may be substituted by one to three halogen atoms mentioned above.

The pharmaceutically acceptable salts of Compounds (I) include pharmaceutically acceptable acid addition salts, metal salts, ammonium salts, organic amine addition salts and amino acid addition salts.

As the pharmaceutically acceptable acid addition salts of Compounds (I), inorganic acid addition salts such as hydrochloride, hydrobromide, sulfate and phosphate, and organic acid addition salts such as acetate, oxalate, malonate, maleate, fumarate, tartrate, succinate and citrate may be mentioned. As the pharmaceutically acceptable metal salts, alkali metal salts such as lithium salt, sodium salt and potassium salt, alkaline earth metal salts such as magnesium salt and calcium salt, aluminium salt, and zinc salt may be mentioned. As the pharmaceutically acceptable ammonium salts, ammonium salt and tetramethylammonium salt may be mentioned. As the pharmaceutically acceptable organic amine addition salts, salts with morpholine and piperidine may be mentioned, and as the pharmaceutically acceptable amino acid addition salts, lysine addition salt may be mentioned.

The processes for preparing Compounds (I) are described below. However, preparation of Compounds (I) is not deemed to be limited to these processes.

In the processes shown below, in cases where the defined groups change under the conditions shown or are inadequate for the practice of the processes, the processes can be easily operated by applying thereto means conventionally used in organic synthetic chemistry, for example, protection of functional groups, removal of protective groups, oxidation, reduction and hydrolysis.

Process 1

Compounds (I) can be prepared in accordance with the following reaction steps:

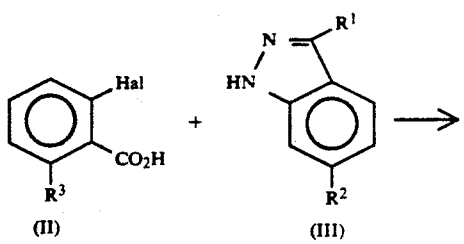

(II)    (III)

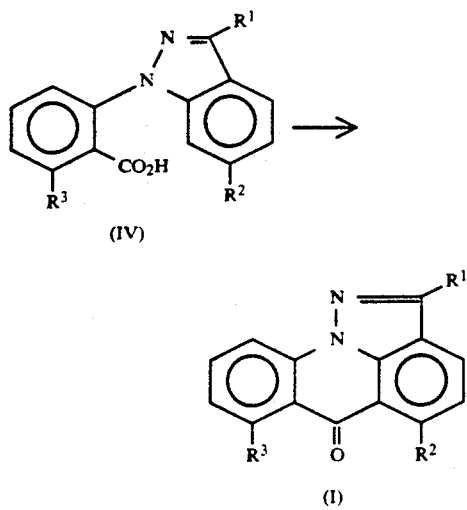

(IV)

(I)

In the above formulae, $R^1$, $R^2$ and $R^3$ have the same meanings as defined above; and Hal represents halogen.

The halogen represented by Hal is chlorine, bromine or iodine.

For the reaction, the 2-halogenobenzoic acid (II) is first heated with an equivalent amount of the indazole (III) in the presence of a base and copper(II) oxide as a catalyst in an inert solvent such as nitrobenzene to obtain Compound (IV). As the base, potassium carbonate, sodium carbonate, lithium carbonate, etc. are preferably used in an amount of 1 to 2 equivalents based on Compound (II). The copper(II) oxide is used in an amount of 0.01 to 0.2 equivalent, preferably 0.05 to 0.1 equivalent, based on Compound (II). The reaction temperature is 120° to 200° C., preferably 150° to 180° C., and the reaction is generally completed in 0.5 to 12 hours.

Compound (IV) obtained is then heated in an acid such as sulfuric acid of polyphosphoric acid to obtain the cyclized Compound (I). When sulfuric acid is used, the amount of the sulfuric acid is 1 to 20 times, preferably 5 to 10 times that of Compound (IV) by weight, and the reaction temperature is 50° to 150° C., preferably 80° to 120° C. When polyphosphoric acid is used, the amount of the acid is 5 to 100 times, preferably 20 to 40 times that of Compound (IV), and the reaction temperature is 80° to 200° C., preferably 120° to 180° C. The reaction is generally completed in 0.5 to 12 hours.

Compounds (II) which are the starting compounds are commercially available or can be prepared by known methods (refer to the publications mentioned in the examples). Compounds (III) can be synthesized in accordance with the methods described in J. Am. Chem. Soc., 74, 2009 (1952) and Chemical Abstracts 65, 2245b (1966) or by modifications thereof.

Some of Compounds (I) obtained by the method described above can be used as intermediates for preparing other novel Compounds (I) by Processes 2 to 9 described below.

Process 2

Synthesis of Compounds (I-1) [Compounds (I) wherein $R^1$ is —$CH_2Hal$]:

Compounds (I-1) can be obtained from Compounds (Ia) [Compounds (I) wherein $R^1$ is $CH_3$ (X=H)] obtained in the above Process 1 in accordance with the following reaction step.

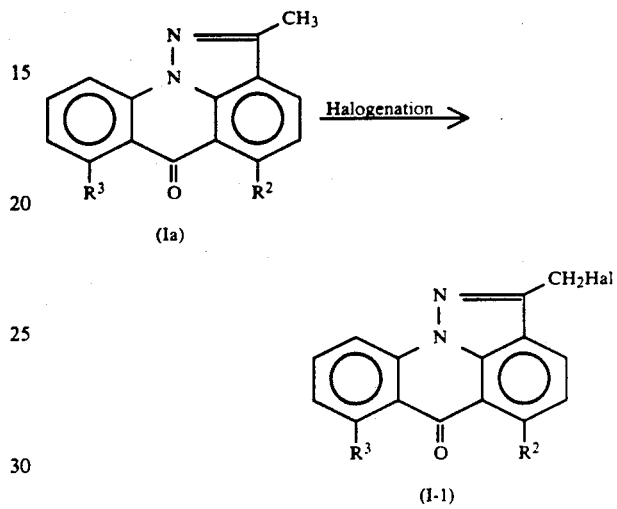

(Ia)

(I-1)

In the formulae, $R^2$, $R^3$ and Hal have the same meanings as defined above.

Compound (Ia) is allowed to react with N-halogenosuccinimide in an amount of 0.9 to 1.1 equivalents based on Compound (Ia) or with 1,3-dibromo-5,5-dimethylhydantoin in an amount of 0.4 to 0.6 equivalent based on Compound (Ia) in the presence or absence of a catalyst in an inert solvent. As the N-halogenosuccinimide, N-chlorosuccinimide and N-bromosuccinimide are preferably used. As the catalyst, if necessary, benzoyl peroxide (BPO) and azobisisobutyronitrile (AIBN) may be used in an amount of 0.01 to 0.1 equivalent based on Compound (Ia). As the inert solvent, carbon tetrachloride is preferably used, and the reaction proceeds at room temperature or with heating under reflux and is generally completed in 0.5 to 24 hours.

Process 3

Synthesis of Compounds (I-2) [Compounds (I) wherein $R^1$ is —$CH_2NR^{4a}R^{4b}$]:

Compounds (I-2) can be obtained from Compounds (I-1) obtained in the above Process 2 and amines (V) in the following manner.

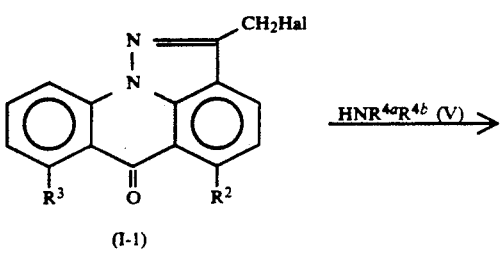

(I-1)

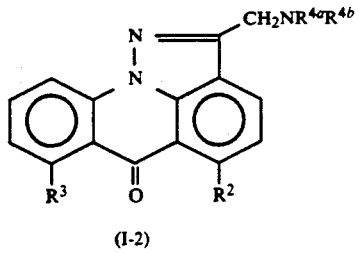

(I-2)

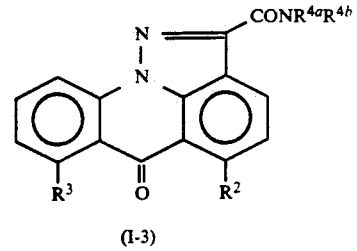

(I-3)

In the formulae, $R^2$, $R^3$, $R^{4a}$, and Hal have the same meanings as defined above.

Compound (I-1) is allowed to react with Compound (V) or its acid addition salt optionally in the presence of a base with or without an inert solvent. In general, Compound (V) is used in an amount of one equivalent to a large excess based on Compound (I-1). When no solvent is used in the reaction, Compound (V) may be used also as a solvent. When Compound (V) is used in the form of acid addition salt (for example, hydrochloride, hydrobromide, acetate, trifluoroacetate and p-toluenesulfonate; the same shall apply hereinafter), an inorganic salt such as potassium hydroxide or sodium carbonate and an organic amine such as triethylamine, tributylamine or pyridine may be used in the reaction as a base in an amount of one equivalent to an excess based on Compound (V). The base may be used also as a solvent in the reaction. When Compound (V) is used in the free form, it is sometimes desirable to carry out the reaction in the presence of said base. As a catalyst, potassium fluoride, sodium fluoride, cesium fluoride, etc. may be used in the reaction in an amount of 0.005 to 0.2 equivalent based on Compound (I-1). As the inert solvent, dimethylformamide, dimethylsulfoxide, tetrahydrofuran, dioxane, chloroform, dichloromethane, methanol, ethanol, tert-butanol, etc. may be used. The reaction may be carried out at room temperature or with cooling or heating, but is preferably carried out at room temperature to 80° C., and is completed in 1 to 24 hours.

Process 4

Synthesis of Compounds (I-3) [Compounds (I) wherein $R^1$ is —$CONR^{4a}R^{4b}$]:

Compounds (I-3) can be obtained from Compounds (Ib) [Compounds (I) wherein R is —COOH (Y=OH)] obtained in the above Process 1 in accordance with the following reaction step.

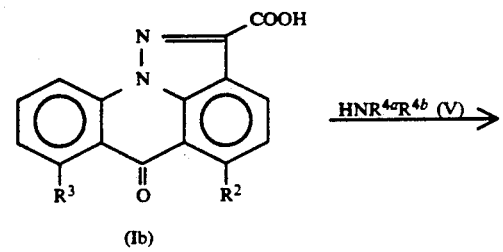

In the formulae, $R^2$, $R^3$, $R^{4a}$ and $R^{4b}$ have the same meanings as defined above.

Compound (Ib) is allowed to react with Compound (V) or its acid addition salt in an amount of 1-2 equivalents based on Compound (Ib) together with a condensing agent in an inert solvent optionally in the presence of a base. As the condensing agent, those which are generally used in the field of peptide chemistry can be used, but 2-chloro-1-methylpyridinium iodide is preferably used. The amount of the condensing agent to be used is equivalent to that of Compound (V), and the reaction is usually carried out in the presence of a base such as triethylamine or tributylamine. The amount of the base to be used is 1 to 3 equivalents based on Compound (Ib). When Compound (V) is used in the form of acid addition salt, an additional amount of the base necessary for converting the salt into free Compound (V) is to be added to the reaction system. As the inert solvent, dimethylformamide, dimethylsulfoxide, tetrahydrofuran, chloroform, dichloromethane, etc. may be used. The reaction is carried out at 0° to 60° C., preferably at room temperature, and is generally completed in 1 to 48 hours.

Process 5

Synthesis of Compounds (I-4) [Compounds (I) wherein $R^1$ is —$COOR^{4d}$]:

Compounds (I-4) can be obtained from Compounds (Ib) [Compounds (I) wherein $R^1$ is —COOH (Y=OH)] obtained in the above Process 1 in accordance with the following reaction step.

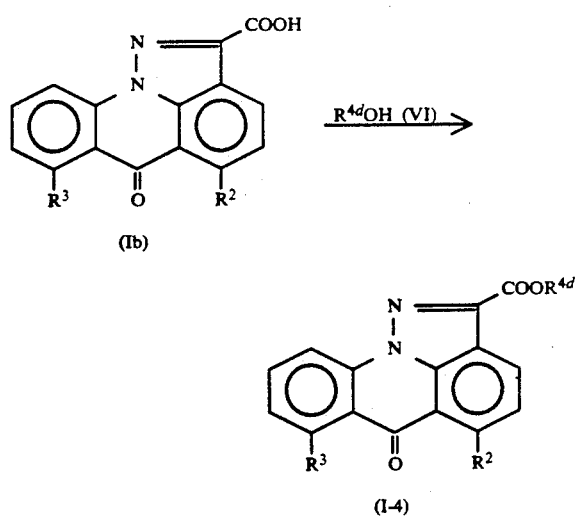

In the formulae, $R^2$ and $R^3$ have the same meanings as defined above; and $R^{4d}$ has the same meaning as $R^4$ except hydrogen.

Compound (Ib) is allowed to react with the alcohol (VI) under the conditions of general esterification. For instance, Compound (VI), which also acts as a solvent, is used in large excess of Compound (Ib), and the reaction is carried out in the presence of an acid catalyst such as hydrochloric acid, sulfuric acid or p-toluenesulfonic acid, generally at a temperature in the range of 50° C. to the boiling point of Compound (VI). The reaction is completed in 1 to 24 hours.

The esterification can also be carried out in the presence of a condensing agent, and use of such condensing agent is more advantageous when $R^{4d}$ in Compound (IV) is alkyl having a substituent such as $-NR^{5a}R^{5b}$. As the condensing agent, 2-chloro-1-methylpyridinium iodide is preferably used, and the reaction can be carried out in the same manner as in Process 4.

Process 6

Synthesis of Compounds (I-5) [Compounds (I) wherein $R^2$ is lower alkanoylamino[:

Compounds (I-5) can be obtained from Compounds (Ic) [Compounds (I) wherein $R^2$ is $-NH_2$] obtained in the above Process 1 in accordance with the following reaction step.

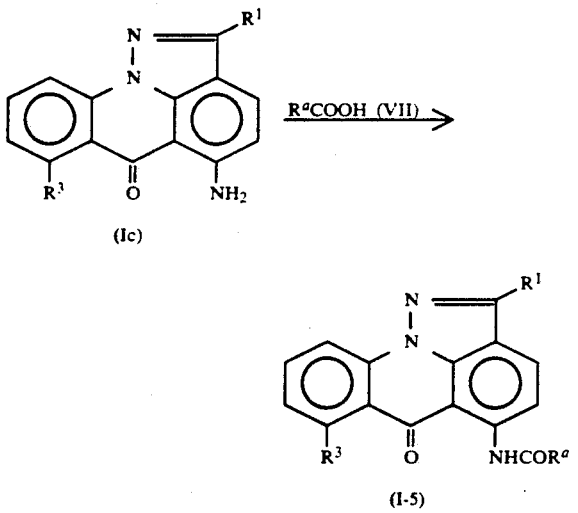

In the formulae, $R^1$ and $R^3$ have the same meanings as defined above; and $R^a$ represents lower alkyl.

The lower alkyl represented by $R^a$ means an optionally halogen-substituted lower alkyl group, and the halogen and the lower alkyl group have the same meanings as in the definitions relating to the above-mentioned formula (I).

The amino compound (Ic) is acylated with the carboxylic acid (VII) or its reactive derivative in an inert solvent optionally in the presence of a base. The reactive derivative of the carboxylic acid includes acid halides such as acid chlorides and acid bromides as well as acid anhydrides. Compound (VII) or its reactive derivative is used in an amount of one equivalent to a large excess based on Compound (Ic), and it can be used also as a solvent. As the base, tertiary amines such as triethylamine and pyridine may be used, and they can be used also as a solvent. As the inert solvent, dimethylformamide, chloroform, dichloromethane, etc. may be used. The reaction may be carried out at room temperature or with cooling or heating, but is generally carried out at room temperature, and is completed in 0.25 to 12 hours.

Process 7

Synthesis of Compounds (I-6) [Compounds (I) wherein $R^2$ is halogen]:

Compounds (I-6) can be obtained from Compounds (Ic) [Compounds (I) wherein $R^2$ is $-NH_2$] obtained in the above Process 1 in accordance with the following reaction step.

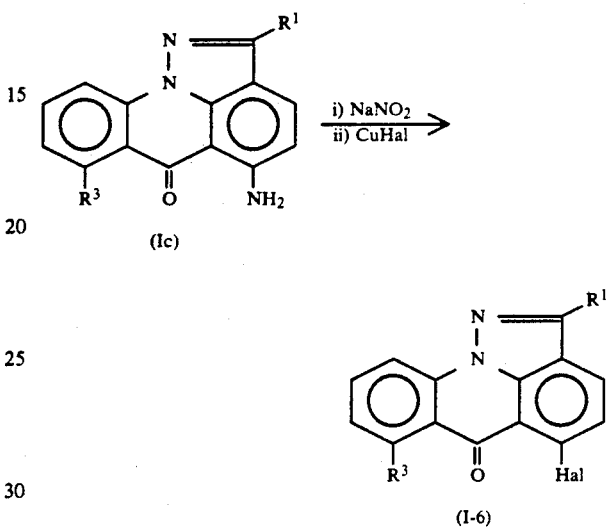

In the formulae, $R^1$, $R^3$ and Hal have the same meanings as defined above.

Compound (Ic) is allowed to react with sodium nitrite to form a diazonium salt, which is then subjected to reaction with copper(I) halide to obtain Compound (I-6). For the reaction, sodium nitrite in an amount of 1 to 1.5 equivalents based on Compound (Ic) is dissolved in water or sulfuric acid, and acetic acid is added thereto with ice-cooling in an amount of 1.5 to 5 times that of the water or sulfuric acid used. Compound (Ic) is added to the mixture, and the reaction temperature is raised to room temperature to obtain the corresponding diazonium salt. The reaction is usually completed in 0.25 to 2 hours. To the resulting reaction mixture is added copper(I) halide in an amount of 1.5 to 3 equivalents based on Compound (IC) with ice-cooling, and then concentrated hydrohalogenic acid is added to the reaction system in the same amount as that of the previously used acetic acid. The reaction is further continued at room temperature or under heating. The reaction is generally carried out at 50° to 100° C. and is completed in 0.25 to 2 hours.

Process 8

Synthesis of Compounds (I-7) [Compounds (I) wherein $R^2$ is $-NR^{4A}R^{4B}$]:

Compounds (I-7) can be obtained from Compounds (I-6) [Compounds (I) wherein $R^2$ is halogen] obtained in the above Process 7 in accordance with the following reaction step.

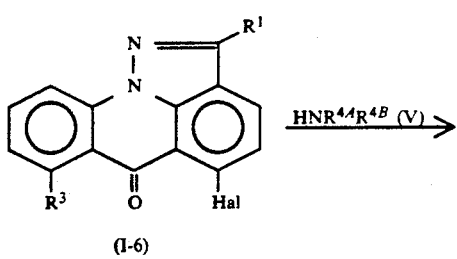
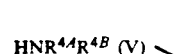

(I-6)

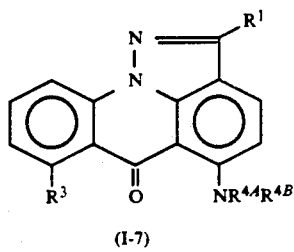

(I-7)

In the formulae, $R^1$, $R^3$, $R^{4A}$, $R^{4B}$ and Hal have the same meanings as defined above.

The reaction can be carried out in the same manner as in Process 3.

Alternatively, Compounds (I-7) wherein —$NR^{4A}R^{4B}$ represents —$NH(CH_2)_2OH$ can also be obtained by reaction of Compound (Ic) with ethylene oxide.

Process 9

Synthesis of Compounds (I-8) [Compounds (I) wherein $R^2$ is —$OR^{4d}$]:

Compounds (I-8) can be obtained from Compounds (I-6) [Compounds (I) wherein $R^2$ is halogen] obtained in the above Process 7 in accordance with the following reaction step.

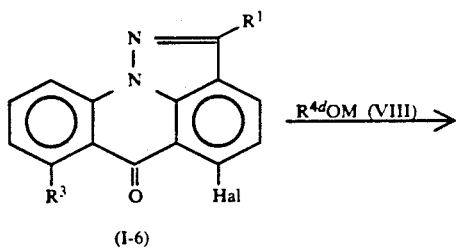
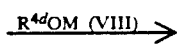

(I-6)

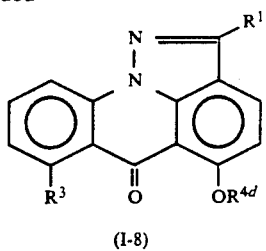

(I-8)

In the formulae, $R^1$, $R^3$, $R^{4d}$ and Hal have the same meanings as defined above; and M represents an alkali metal.

The alkali metal represented by M is lithium, sodium or potassium.

Compound (I-6) is allowed to react with Compound (VIII) in an amount of 1 to 6 equivalents based on Compound (I-6) in a lower alcohol such as $R^{4d}OH$ or a solvent mixture comprising an alcohol and an inert solvent such as dioxane, tetrahydrofuran or 1,2-dimethoxyethane, at room temperature to 70° C. The reaction is completed in 0.5 to 18 hours.

Process 10

Process of Compounds (I-9) [Compounds (I) wherein $R^2$ and/or $R^3$ is —OH]:

Compounds (I-9) can be obtained by hydrolyzing Compounds (I-10) which are Compounds (I) wherein the corresponding group(s) of $R^2$ and/or $R^3$ is the above-mentioned lower alkoxyl or benzyloxy.

For the reaction, Compound (I-10) is treated with a large excess of hydrochloric acid or hydrobromic acid, which acts also as solvent optionally together with acetic acid, at a temperature in the range of 50° C. to the boiling point of the solvent. The reaction is completed in 1 to 24 hours.

Compounds (I) having desired functional groups at the desired positions can be obtained by properly combining the above-described Processes 1 to 10.

The intermediates and the final products obtainable in the above processes can be isolated and purified by conventional purification methods which are generally utilized in the field of organic synthetic chemistry, for example, by filtration, extraction, washing, drying, concentration, recrystallization and various kinds of chromatography.

Typical examples of Compounds (I) of the present invention are shown in Table 1 below. The compound numbers in Table 1 respectively correspond to example numbers.

TABLE 1

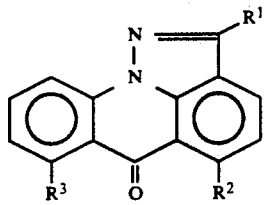

| Compound No. | $R^1$ | $R^2$ | $R^3$ |
|---|---|---|---|
| 1 | COOH | H | H |
| 2 | $CH_3$ | H | H |
| 3 | $CONH(CH_2)_2N(CH_3)_2$ | H | H |
| 4 | $CONH(CH_2)_2N(CH_3)_2$ | H | $OCH_3$ |

TABLE 1-continued

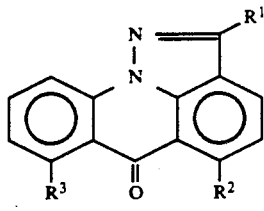

| Compound No. | R¹ | R² | R³ |
|---|---|---|---|
| 5 | CONH(CH$_2$)$_2$N⟨morpholine⟩ | H | H |
| 6 | CH$_2$Br | H | H |
| 7 | CH$_2$N(CH$_2$CH$_2$OH)$_2$ | H | H |
| 8 | CH$_2$NH(CH$_2$)$_2$N⟨morpholine⟩ | H | H |
| 9 | CH$_2$N(CH$_2$CH$_2$Cl)$_2$ | H | H |
| 10 | CH$_2$NH(CH$_2$)$_2$N(CH$_3$)$_2$ | H | H |
| 11 | CH$_3$ | NH$_2$ | H |
| 12 | CH$_3$ | NHCOCF$_3$ | H |
| 13 | CH$_3$ | NHCOCH$_3$ | H |
| 14 | CH$_2$Br | NHCOCF$_3$ | H |
| 15 | CH$_2$NH(CH$_2$)$_2$NH$_2$ | NH$_2$ | H |
| 16 | CH$_2$NH(CH$_2$)$_2$NH(CH$_2$)$_2$OH | NH$_2$ | H |
| 17 | CH$_2$NH(CH$_2$)$_2$N⟨morpholine⟩ | NH$_2$ | H |
| 18 | CH$_2$NH(CH$_2$)$_2$N(CH$_3$)$_2$ | NH$_2$ | H |
| 19 | CH$_3$ | NH(CH$_2$)$_2$OH | H |
| 20 | CH$_2$Br | Br | H |
| 21 | CH$_2$NH(CH$_2$)$_2$NH$_2$ | NH(CH$_2$)$_2$NH$_2$ | H |
| 22 | CH$_2$NH(CH$_2$)$_3$NH$_2$ | NH(CH$_2$)$_3$NH$_2$ | H |
| 23 | CH$_2$NH(CH$_2$)$_2$N(CH$_3$)$_2$ | NH(CH$_2$)$_2$N(CH$_3$)$_2$ | H |
| 24 | CH$_2$Br | Br | OCH$_3$ |
| 25 | CH$_2$NH(CH$_2$)$_2$NH$_2$ | NH(CH$_2$)$_2$NH$_2$ | OCH$_3$ |
| 26 | CH$_2$NH(CH$_2$)$_3$NH$_2$ | NH(CH$_2$)$_3$NH$_2$ | OCH$_3$ |
| 27 | CH$_2$NH(CH$_2$)$_2$N(CH$_3$)$_2$ | NH(CH$_2$)$_2$N(CH$_3$)$_2$ | OCH$_3$ |
| 28 | CH$_2$NH(CH$_2$)$_2$NH$_2$ | NH(CH$_2$)$_2$NH$_2$ | OH |
| 29 | CH$_2$NH(CH$_2$)$_3$NH$_2$ | NH(CH$_2$)$_3$NH$_2$ | OH |
| 30 | CH$_2$NH(CH$_2$)$_2$N(CH$_3$)$_2$ | NH(CH$_2$)$_2$N(CH$_3$)$_2$ | OH |
| 31 | CO$_2$(CH$_2$)$_2$N(CH$_3$)$_2$ | H | H |
| 32 | CH$_2$NH(CH$_2$)$_3$NHCH$_3$ | NH(CH$_2$)$_3$NHCH$_3$ | H |
| 33 | CH$_2$NH(CH$_2$)$_2$NHCH$_3$ | NH(CH$_2$)$_2$NHCH$_3$ | H |
| 34 | CH$_2$NH(CH$_2$)$_2$NHC$_2$H$_5$ | NH(CH$_2$)$_2$NHC$_2$H$_5$ | H |
| 35 | CH$_2$NH(CH$_2$)$_2$N⟨morpholine⟩ | NH(CH$_2$)$_2$N⟨morpholine⟩ | H |
| 36 | CH$_2$NH(CH$_2$)$_2$N(C$_2$H$_5$)$_2$ | NH(CH$_2$)$_2$N(C$_2$H$_5$)$_2$ | H |
| 37 | CH$_2$NH(CH$_2$)$_4$NH$_2$ | NH(CH$_2$)$_4$NH$_2$ | H |
| 38 | CH$_2$N(CH$_3$)(CH$_2$)$_2$NH$_2$ | NH(CH$_2$)$_2$NHCH$_3$ | H |
| 39 | CH$_2$NH(CH$_2$)$_3$N(CH$_3$)$_2$ | NH(CH$_2$)$_3$N(CH$_3$)$_2$ | H |
| 40 | CH$_2$NH(CH$_2$)$_2$N(CH$_3$)$_2$ | Br | OCH$_3$ |
| 41 | CH$_2$NH(CH$_2$)$_2$N(CH$_3$)$_2$ | NH(CH$_2$)$_2$NH(CH$_2$)$_2$OH | OCH$_3$ |
| 42 | CH$_2$NH(CH$_2$)$_2$N(CH$_3$)$_2$ | NH(CH$_2$)$_2$NH(CH$_2$)$_2$OH | OH |
| 43 | CH$_2$NH(CH$_2$)$_2$NH$_2$ | Br | OCH$_3$ |
| 44 | CH$_2$NH(CH$_2$)$_2$NH$_2$ | Br | OH |
| 45 | CH$_2$NH(CH$_2$)$_2$NH$_2$ | NH(CH$_2$)$_2$NH(CH$_2$)$_2$OH | OCH$_3$ |
| 46 | CH$_2$NH(CH$_2$)$_2$NH$_2$ | NH(CH$_2$)$_2$NH(CH$_2$)$_2$OH | OH |

TABLE 1-continued

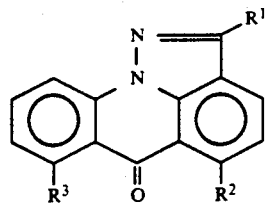

| Compound No. | R¹ | R² | R³ |
|---|---|---|---|
| 47 | $CH_2NH(CH_2)_2NH_2$ | $NH(CH_2)_2NH(CH_2)_2NH_2$ | $OCH_3$ |
| 48 | $CH_2NH(CH_2)_2NH_2$ | $NH(CH_2)_2NH(CH_2)_2NH_2$ | $OH$ |
| 49 | $CH_2N(CH_2CH_2OH)_2$ | $Br$ | $OCH_3$ |
| 50 | $CH_2N(CH_2CH_2OH)_2$ | $NH(CH_2)_2N(CH_3)_2$ | $OCH_3$ |
| 51 | $CH_2N(CH_2CH_2OH)_2$ | $NH(CH_2)_2N(CH_3)_2$ | $OH$ |
| 52 | $CH_2N(CH_2CH_2OH)_2$ | $NH(CH_2)_2NH_2$ | $OCH_3$ |
| 53 | $CH_2N(CH_2CH_2OH)_2$ | $NH(CH_2)_2NH_2$ | $OH$ |
| 54 | $CH_2N(CH_2CH_2Cl)_2$ | $NH(CH_2)_2N(CH_3)_2$ | $OCH_3$ |
| 55 | $CH_2Br$ | $Br$ | $OH$ |
| 56 | $CH_2NH(CH_2)_2N\!\!\diagup\!\!\diagdown\!\!O$ | $NH(CH_2)_2N\!\!\diagup\!\!\diagdown\!\!O$ | $OH$ |
| 57 | $CH_2NH(CH_2)_2S(CH_2)_2OH$ | $Br$ | $OH$ |
| 58 | $CH_2NH(CH_2)_2S(CH_2)_2OH$ | $NH(CH_2)_2S(CH_2)_2OH$ | $OH$ |
| 59 | $CH_2NH(CH_2)_2S(CH_2)_2OH$ | $NH(CH_2)_2NH_2$ | $OH$ |
| 60 | $CH_2NH(CH_2)_2O(CH_2)_2OH$ | $Br$ | $OH$ |
| 61 | $CH_2NH(CH_2)_2O(CH_2)_2OH$ | $NH(CH_2)_2O(CH_2)_2OH$ | $OH$ |
| 62 | $CH_2NH(CH_2)_2O(CH_2)_2OH$ | $NH(CH_2)_2NH_2$ | $OH$ |
| 63 | $CH_2NH(CH_2)_2O(CH_2)_2OH$ | $NH(CH_2)_3NH_2$ | $OH$ |
| 64 | $CH_2NH(CH_2)_2O(CH_2)_2OH$ | $NH(CH_2)_2N(CH_3)_2$ | $OH$ |
| 65 | $CH_2NH(CH_2)_2O(CH_2)_2OH$ | $NH(CH_2)_2NHCH_3$ | $OH$ |
| 66 | $CH_2NH(CH_2)_2O(CH_2)_2OH$ | $NH(CH_2)_2NH(CH_2)_2OH$ | $OH$ |
| 67 | $CH_2NH(CH_2)_2OH$ | $Br$ | $OH$ |
| 68 | $CH_2NH(CH_2)_2OH$ | $NH(CH_2)_2NH_2$ | $OH$ |
| 69 | $CH_2NH(CH_2)_2OH$ | $NH(CH_2)_2OH$ | $OH$ |
| 70 | $CH_2NH(CH_2)_3N(CH_3)_2$ | $NH(CH_2)_3N(CH_3)_2$ | $OH$ |
| 71 | $CH_2N(CH_2CH_3)_2$ | $NH(CH_2)_2N(CH_3)_2$ | $OH$ |
| 72 | $CH_3$ | $OCH_3$ | $H$ |
| 73 | $CH_2Br$ | $OCH_3$ | $H$ |
| 74 | $CH_2Br$ | $OH$ | $H$ |
| 75 | $CH_2NH(CH_2)_2NH_2$ | $OCH_3$ | $H$ |
| 76 | $CH_2NH(CH_2)_2NH_2$ | $OH$ | $H$ |
| 77 | $CH_2N(CH_2CH_2OH)_2$ | $OCH_3$ | $H$ |
| 78 | $CH_2N(CH_2CH_2Cl)_2$ | $OCH_3$ | $H$ |
| 79 | $CH_2S(CH_2)_2NH_2$ | $NH(CH_2)_2NH_2$ | $H$ |
| 80 | $CH_2S(CH_2)_2NH_2$ | $NH(CH_2)_2N(CH_3)_2$ | $H$ |
| 81 | $CH_2NH(CH_2)_2NH_2$ | $OCH_3$ | $OCH_3$ |
| 82 | $CH_2N(CH_2CH_2OH)_2$ | $OCH_3$ | $OCH_3$ |
| 83 | $CH_2NH(CH_2)_2NH_2$ | $OH$ | $OH$ |
| 84 | $CH_2N(CH_2CH_2OH)_2$ | $OH$ | $H$ |

The anti-tumor activity of the compounds of the present invention is shown below referring to experimental examples.

EXPERIMENTAL EXAMPLE 1

Inhibitory effect on growth of human cancer cells ($HeLaS_3$):

HeLaS, cells were suspended in a medium comprising MEM medium (Nissui Pharmaceutical Co., Ltd.) and 2 mM glutamine (hereinafter referred to as Medium A) to a concentration of $3 \times 10^4$ cells/ml. The cell suspension thus prepared was put into wells of a 96-well microtiter plate in an amount of 0.1 ml/well. The cells on the plate were incubated in a $CO_2$-incubator at 37° C. for 20 hours, and 0.05 ml of a sample containing a test compound and appropriately diluted with Medium A was added to each well. The cells were further incubated in the $CO_2$-incubator at 37° C. for 72 hours. After the culture supernatant was removed, a medium comprising Medium A and 0.02% Neutral Red was added to the residue in an amount of 0.1 ml/well, followed by incubation at 37° C. for one hour in the $CO_2$-incubater, whereby the cells were stained. The culture supernatant was removed and the residue was washed once with physiological saline solution. The pigment was extracted with 0.001 N-HCl/30%-ethanol, and the absorbance was determined at 550 nm with a microplate reader. The absorbance determined for intact cells was compared with that for the cells treated with the test compound of a known concentration, and the concentration of the test compound for inhibiting 50% growth of the cells ($IC_{50}$) was calculated. The results obtained are shown in Table 2.

TABLE 2

| Compound No. | $IC_{50}$ (μg/ml) |
|---|---|
| 3 | 2.5 |

TABLE 2-continued

| Compound No. | IC$_{50}$ (μg/ml) |
|---|---|
| 4 | 2.98 |
| 5 | 7.2 |
| 7 | 8.89 |
| 8 | 4.9 |
| 9 | 0.92 |
| 11 | 2.16 |
| 15 | 0.71 |
| 16 | 0.87 |
| 17 | 1.96 |
| 21 | 0.17 |
| 22 | 0.078 |
| 23 | 0.55 |
| 25 | 7.65 |
| 26 | 0.22 |
| 28 | 0.0023 |
| 29 | 0.014 |
| 30 | 0.056 |
| 32 | 1.16 |
| 33 | 2.69 |
| 34 | 1.72 |
| 35 | 3.37 |
| 36 | 3.10 |
| 37 | 2.11 |
| 38 | 2.89 |
| 39 | 8.33 |
| 42 | 0.12 |
| 46 | 0.0030 |
| 48 | 0.0026 |
| 51 | 0.023 |
| 56 | 0.26 |
| 62 | 0.0023 |
| 68 | 0.00075 |
| 69 | 0.0026 |
| Adriamycin | 0.009–0.05 |

EXPERIMENTAL EXAMPLE 2

Effect on P388 ascites tumor:

P388 tumor cells (10$^6$ cells) were implanted intraperitoneally into a DBA/2 mouse and the cells were collected from the ascitic fluid of the animal 7 days after the implantation. The cells were ashed once with sterilized physiological saline solution and then suspended in a sterilized physiological saline solution to prepare a cell suspension containing 5×10$^6$ cells/ml. The suspension (0.2 ml) was intraperitoneally inoculated into a male CDF$_1$ mouse aged 6 weeks. A test compound was dissolved in physiological saline solution and intraperitoneally administered to the animal 24 hours after implantation of the tumor cells. One test group comprised 5 mice. The mean survival time (days) of a test group which received a test compound at a specified concentration was calculated as T from survival days of animals in the group. ON the other hand, the mean survival time (days) of the non-administered group (C) was obtained in the same manner, and the increased life span (ILS %) was calculated as [(T-C)/C]×100 (%). The results obtained are shown in Table 3.

TABLE 3

| Compound No. | Dose (mg/kg) | ILS (%) |
|---|---|---|
| 9 | 18.8 | 28 |
| 21 | 37.5 | 50 |
| 22 | 25 | 52 |
| 23 | 50 | 46 |
| 25 | 25 | 39 |
| 26 | 25 | 28 |
| 28 | 12.5 | >154 |
| 29 | 12.5 | >121 |
| 30 | 50 | 61 |
| 46 | 25 | >156 |
| 48 | 50 | >200 |

TABLE 3-continued

| Compound No. | Dose (mg/kg) | ILS (%) |
|---|---|---|
| 51 | 25 | >186 |
| 53 | 25 | >100 |
| 56 | 100 | 121 |
| 59 | 12.5 | >134 |
| 66 | 12.5 | >133 |
| 67 | 75 | 31 |
| 70 | 12.5 | >112 |
| Mitomycin C | 4–6 | 57–67 |

EXPERIMENTAL EXAMPLE 3

A test compound was administered intravenously once to male ddy mice. One test group comprised ten mice. After the administration, the animals were observed for 14 days and deaths were noted. LD50 was calculated from the death rate of each group in accordance with Probit's method. The results obtained are shown in Table 4.

TABLE 4

| Compound No. | LD$_{50}$ (mg/kg) |
|---|---|
| 28 | 15.7 |
| 51 | 15.7 |
| 53 | 25.0 |

The compounds of the present invention have an excellent anti-tumor activity and are useful as anti-tumor agents. The term "tumor" as used in this application includes leukemia, stomach, intestinum crassum, lung, breast and uterine tumors found in mammals including humans.

Compounds (I) and their pharmaceutically acceptable salts can be administered directly or in the form of various pharmaceutical preparations. For instance, when they are used in the form of an injection, they are dissolved in a diluent which is generally used in this technical field such as physiological saline solution or glucose, lactose or mannitol solution for injection. Alternatively, the compounds may be freeze-dried in accordance with the Japanese Pharmacopoeia or may be prepared into injectable powder by adding sodium chloride thereto. In addition, the injection may also contain an auxiliary agent such as polyethylene glycol or HCO-60 (surfactant, manufactured by Nikko Chemical Co., Ltd.), ethanol and/or a carrier such as liposome or cyclodextrin. The injection is usually used for intravenous administration, but can also be administered intramuscularly, intra-arterially, intraperitoneally or intrathoracically.

Compounds (I) and their salts may be formed into tablets, granules, powder or syrup for oral administration with a suitable excipient, disintegrator, binder or lubricant in a conventional manner. Further, Compounds (I) and their salts may be mixed with a conventional carrier and formed into suppositories for rectal administration in a conventional manner.

Dosage may appropriately vary according to the kind of Compounds (I) or their salts as well as the age and condition of a patient, but is generally 0.5 to 75 mg/60 kg/day as Compound (I) for mammals including humans. Administration schedule can also be varied according to the condition of a patient and the dosage. For example, the preparation can be intermittently administered once a week or once every three weeks.

The anti-tumor compositions of the present invention are expected to be effective against leukemia, stomach cancer, intestinum crassum cancer, lung cancer, breast cancer, uterine cancer, etc. of mammals including humans.

Certain embodiments of the invention are illustrated in the following examples.

EXAMPLE 1

2-Carboxy-6H-pyrazolo[4,5,1-d,e]acridin-6-one (Compound 1):

3-Indazolecarboxylic acid (4.10 g), 3.90 g of 2-chlorobenzoic acid, 3.90 g of potassium carbonate and 0.18 g of copper(II) oxide were stirred in 150 ml of nitrobenzene at 170° to 180° C. for 3 hours. After cooling, 100 ml of water was added to the reaction mixture, and the insoluble substance was removed by filtration. The resulting solution was washed with chloroform, and the aqueous layer was decolored with active charcoal and then filtered. The filtrate was made acidic with 50 ml of 1N hydrochloric acid and then extracted with chloroform. The chloroform layer was dried over anhydrous sodium sulfate and concentrated under reduced pressure. The residue was crystallized from methanol-chloroform-ether to obtain 2.13 g (30.2%) of 1-(2-carboxyphenyl)-3-indazolecarboxylic acid.

To 1.06 g of the obtained compound was added 27 g of polyphosphoric acid and the mixture was stirred at 120° to 130° C. for 3.5 hours. After cooling, water was added to the reaction mixture and the crystals precipitated were separated by filtration, whereby 0.89 g (89.9%) of Compound 1 was obtained. Two hundred mg of the compound was dissolved in 30 ml of dimethylformamide, and 0.16 g of powdery sodium methoxide was added thereto. The crystals precipitated were separated by filtration and recrystallized from methanol to obtain the sodium salt of Compound 1.

m.p. (° C.): >300

Elementary analysis (%): Calcd. for $C_{15}H_7N_2O_3 \cdot Na \cdot 2.1H_2O$: C, 55.60; H, 3.48; N, 8.64; Found: C, 55.44; H, 3.27; N, 8.76

NMR (CDCl$_3$/DMSO-d$_6$) δ(ppm): 7.55(1H, t, J=7.4 Hz), 7.75(1H, t, J=7.7 Hz), 7.89(1H, t, J=7.4 Hz), 8.39 (1H, d, J=7.4 Hz), 8.42(1H, d, J=7.7 Hz), 8.45(1H, d, J=7.4 Hz), 8.59(1H, d, J=7.7 Hz)

IR (KBr) cm$^{-1}$: 3430, 1650, 1603, 1506, 1464, 1425

EXAMPLE 2

2-Methyl-6H-pyrazolo[4,5,1-d,e]acridin-6-one (Compound 2):

3-Methylindazole (3.30 g), 3.92 g of 2-chlorobenzoic acid, 3.82 g of potassium carbonate and 0.18 g of copper(II) oxide were subjected to reaction in the same manner as in Example 1 to obtain 4.58 g (72.7%) of 1-(2-carboxyphenyl)-3-methylindazole.

To the obtained compound was added 120 g of polyphosphoric acid, and the mixture was stirred at 130° to 150° C. for 6 hours and then at 170° to 180° C. for 5 hours. After cooling, water and chloroform were added to the reaction mixture for extraction, and the chloroform layer was washed with water, dried over anhydrous sodium sulfate and concentrated under reduced pressure. The residue was subjected to silica gel column chromatography with n-hexane-ethyl acetate (1:1) as the eluent and then crystallized from chloroform-ethyl acetate-ether to obtain 2.17 g (51.0%) of Compound 2.

m.p. (° C.): 176 to 178

Elementary analysis (%): Calcd. for $C_{15}H_{10}N_2O$: C, 76.91; H, 4.30; N, 11.96; Found: C, 76.94; H, 4.22; N, 11.96

NMR (CDCl$_3$)δ(ppm): 2.75(3H, s), 7.35(1H, t, J=7.6 Hz), 7.40(1H, dt, J=1.7, 7.7 Hz), 7.7(1H, dt, J=1.4, 7.7 Hz), 8.05(1H, dd, J=0.6, 7.8 Hz), 8.17(1H, dd, J=0.8, 8.3 Hz), 8.35(1H, dd, J=0.7, 7.5 Hz), 8.46 (1H, dd, J=1.4, 8.0 Hz).

IR (KBr) cm$^{-1}$: 1664, 1608, 1522, 1496, 1470, 1442

EXAMPLE 3

2-(2-Dimethylaminoethyl)aminocarbonyl-6H-pyrazolo[4,5,1-d,e]acridin-6-one (Compound 3):

Compound 1 (132 mg) and 140 mg of 2-chloro-1-methylpyridinium iodide were suspended in 10 ml of dimethylformamide, and 0.153 ml of triethylamine and then 0.060 ml of N,N-dimethylethylenediamine were added thereto, followed by stirring at room temperature for 3 hours. The reaction mixture was concentrated under reduced pressure, and methanol was added to the residue. The solid formed was separated by filtration and recrystallized from chloroform-methanol to obtain 64.0 mg (41.7%) of Compound 3. The compound was converted into its hydrochloride in a conventional manner using hydrogen chloride-containing ether solution.

m.p. (° C.): 287 to 289

Elementary analysis (%): Calcd. for $C_{19}H_{18}N_4O_2 \cdot HCl \cdot 0.8H_2O$: C, 59.13; H, 5.01; N, 14.47; Found: C, 59.13; H, 5.01; N, 14.47

NMR (D$_2$O) δ(ppm): 3.1(6H, s), 3.51(2H, t, J=6.4 Hz), 3.82(2H, t, J=6.4 Hz), 7.13(1H, t, J=7.7 Hz), 7.17 (1H, d, J=7.9 Hz), 7.22(1H, t, J=7.6 Hz), 7.43(1H, d, J=7.3 Hz), 7.52(1H, t, J=7.7 Hz), 7.55(1H, d, J=7.7 Hz), 7.71(1H, d, J=7.7 Hz);

IR (KBr) cm$^{-1}$: 1667, 1650, 1604, 1542, 1504, 1488, 1436.

EXAMPLE 4

7-Methoxy-2-(2-dimethylaminoethyl)aminocarbonyl-6H-pyrazolo[4,5,1-d,e]acridin-6-one (Compound 4):

3-Indazolecarboxylic acid (1.16 g), 0.81 g of 2-bromo-6-methoxybenzoic acid [described in Chem. Ber., 107, 3874 (1974)], 0.79 g of potassium carbonate and 0.04 g of copper(II) oxide were subjected to reaction in the same manner as in Example 1 to obtain 0.40 g (25.6%) of 1-(2-carboxy-3-methoxyphenyl)-3-indazolecarboxylic acid.

To the obtained compound was added 20 g of polyphosphoric acid, and the mixture was subjected to reaction also in the same manner as in Example 1 to obtain 0.35 g (93.0%) of 2-carboxy-7-methoxy-6H-pyrazolo[4,5,1-d,e]acridin-6-one.

The resulting compound (118 mg) was allowed to react with 112 mg of N,N-dimethylethylenediamine in the same manner as in Example 3 to obtain 88 mg (54.9%) of Compound 4. The compound was converted into its hydrochloride in a conventional manner.

m.p. (° C.): 250 to 251

Elementary analysis (%): Calcd. for $C_{20}H_{20}N_4O_3 \cdot 1.9HCl$: C, 55.39; H, 5.09; N, 12.92; Found: C, 55.31; H, 4.86; N, 12.89

NMR (CD$_3$OD/DMSO-d$_6$) δ(ppm): 2.90(6H, s), 3.39(2H, t, J=5.4 Hz), 3.77(2H, q, J=5.4 Hz), 3.98(3H, s), 7.20 (1H, dd, J=3.3, 6.5 Hz), 7.76(1H, t, J=7.7 Hz), 7.88-7.95(2H, m), 8.24(1H, d, J=6.8 Hz), 8.52(1H, d, J=7.3 Hz)

IR (KBr) cm$^{-1}$: 1657, 1634, 1604, 1542, 1505, 1467

EXAMPLE 5

2-(2-Morpholinoethyl)aminocarbonyl-6H-pyrazolo[4,5,1-d,e]acridin-6-one (Compound 5):

Compound 1 (132 mg) was allowed to react with mg of 4-(2-aminoethyl)morpholine in the same manner as in Example 3 to obtain 85 mg (60.0%) of Compound 5.

The compound was converted into its hydrochloride in a conventional manner.

m.p. (° C.): 282 to 283

Elementary analysis (%): Calcd. for $C_{21}H_{20}N_4O_3 \cdot HCl \cdot 1.6H_2O$: C, 57.10; H, 5.52; N, 12.68; Found C, 56.93; H, 5.15; N, 12.85

NMR ($D_2O$) δ(ppm): 3.47(2H, t, J=6.3 Hz), 3.54(4H, m), 3.75(2H, t, J=6.4 Hz), 4.08(4H, m), 6.92(1H, t, J=7.7 Hz), 6.95(1H, t, J=7.7 Hz), 7.08(1H, t, J=7.4 Hz), 7.22(1H, d, J=7.1 Hz), 7.36(1H, d, J=7.7 Hz), 7.37(1H, d, J=7.7 Hz), 7.49(1H, d, J=7.7 Hz)

IR (KBr) $cm^{-1}$: 1672, 1651, 1604, 1542, 1504, 1470

EXAMPLE 6

2-Bromomethyl-6H-pyrazolo[4,5,1-d,e]acridin-6-one (Compound 6):

Compound 2 (1.20 g), 1.00 g of N-bromosuccinimide and 0.06 g of benzoyl peroxide were heated under reflux in 120 ml of carbon tetrachloride for 6 hours with stirring. After cooling, the reaction mixture was concentrated to about 12 ml under reduced pressure and then allowed to stand at 3° to 5° C. overnight. The solid formed was separated by filtration and recrystallized from chloroform-carbon tetrachloride to obtain 1.57 g (95.6%) of Compound 6.

m.p. (° C.): 199 to 201

Elementary analysis (%): Calcd. for $C_{15}H_9BrN_2O \cdot 0.4H_2O$: C, 56.24; H, 3.08; N, 8.74; Found: C, 56.34; H, 2.81; N, 8.50

NMR ($CDCl_3$) δ(ppm): 4.79(2H, s), 7.47(1H, dt, J=1.1, 8.2 Hz), 7.66(1H, t, J=7.7 Hz), 7.83(1H, dt, J=1.5, 8.6 Hz), 8.24(1H, dd, J=0.8, 8.3 Hz), 8.29(1H, dd J=0.7, 7.9 Hz), 8.44(1H, dd, J=0.7, 7.5 Hz), 8.50 (1H, dd, J=1.5, 8.1 Hz)

IR (KBr) $cm^{-1}$: 1670, 1607, 1511, 1490, 1470, 1437

EXAMPLE 7

2-Bis(2-hydroxyethyl)aminomethyl-6H-pyrazolo[4,5,1-d,e]acridin-6-one (Compound 7):

Compound 6 (100 mg) and 330 mg of diethanolamine were stirred in 10 ml of chloroform at room temperature overnight. The reaction mixture was concentrated under reduced pressure and the residue was crystallized from ethanol-acetone.

By recrystallization from ethanol-acetone, 34 mg (31.5%) of Compound 7 was obtained.

m.p. (° C.): 138 to 140

Elementary analysis (%): Calcd. for $C_{19}H_{19}N_3O_3 \cdot 0.1 H_2O$: C, 67.28; H, 5.70; N, 12.39; Found: C, 67.41; H, 5.57; N, 12.46

NMR (DMSO-$d_6$) δ(ppm): 2.68-2.72(4H, m), 3.54-3.56(4H, m), 4.26(2H, s), 7.53(1H, dt, J=0.9, 8.1 Hz), 7.71(1H, t, J=7.6 Hz), 7.96(1H, dt, J=1.3, 7.8 Hz), 8.23(1H, d, J=8.1 Hz), 8.34(1H, d, J=7.3 Hz), 8.36, (1H, dd, J=1.4, 8.1 Hz), 8.58(1H, d, J=7.7 Hz)

IR (KBr) $cm^{-1}$: 3300, 1654, 1607, 1520, 1491, 1471, 1434

EXAMPLE 8

2-(2-Morpholinoethyl)aminomethyl-6H-pyrazolo[4,5,1-d,e]acridin-6-one (Compound 8):

Compound 6 (100 mg) and 0.42 ml of 4-(2-aminoethyl)morpholine were subjected to reaction in the same manner as in Example 7 to obtain the desired compound.

The compound was dissolved in methanol, and 0.35 g of 25% hydrobromic acid/acetic acid solution was added thereto, followed by stirring at room temperature for 0.5 hour. The reaction mixture was concentrated under reduced pressure and the residue was crystallized from methanol to obtain 85 mg (50.7%) of the hydrobromide of Compound 8.

m.p. (° C.): 250 to 253

Elementary analysis (%): Calcd. for $C_{21}H_{22}N_4O_2 \cdot 2HBr \cdot 0.8H_2O$: C, 46.83; H, 4.79; N, 10.40; Found: 46.91; H 4.71; N, 10.26

NMR ($D_2O$) δ(ppm): 3.50(4H, t, J=4.8 Hz), 3.70-3.75(2H, m), 3.81-3.86(2H, m), 4.04(4H, t, J=4.8 Hz), 4.82 (2H, s), 7.21(1H, dt, J=1.3, 7.5 Hz), 7.39(1H, t, J=7.7 Hz), 7.62(1H, dt, J=1.1, 7.6 Hz), 7.69(2H, d, J=8.2 Hz), 7.80(1H, d, J=7.2 Hz), 8.07(1H, d, J=7.5 Hz)

IR (KBr) $cm^{-1}$: 1657, 1605, 1517, 1492, 1469

EXAMPLE 9

2-Bis(2-chloroethyl)aminomethyl-6H-pyrazolo[4,5,1-d,e]acridin-6-one (Compound 9):

Compound 7 (64 mg) was allowed to react with 1 ml of thionyl chloride at 60 to 70° C. for 10 minutes. Thionyl chloride was removed from the reaction mixture under reduced pressure and the residue was dissolved in methanol. The solution was decolored with active charcoal and filtered. The resulting filtrate was concentrated and the residue was crystallized from tert-butanol to obtain 62 mg (87%) of the hydrochloride of Compound 9.

m.p. (° C.): 192 to 194

Elementary analysis (%): Calcd. for $C_{19}H_{18}Cl_2N_3O \cdot HCl \cdot 0.5H_2O$: C, 54.37; H, 4.56; N, 10.01; Found: C, 54.33; H, 4.26; N, 9.63

NMR (DMSO-$d_6$) δ(ppm): 3.20(4H, m), 3.88(4H, m), 4.56 (2H, s), 7.56(1H, t, J=7.5 Hz), 7.75(1H, t, J=7.7 Hz), 7.98(1H, t, J=7.4 Hz), 8.25(1H, d, J=8.4 Hz), 8.37(2H, d, J=7.5 Hz), 8.60(1H, d, J=7.7 Hz)

IR (KBr) $cm^{-1}$: 1657, 1606, 1513, 1471

EXAMPLE 10

2-(2-Dimethylaminoethyl)aminomethyl-6H-pyrazolo[4,5,1-d,e]acridin-6-one (Compound 10):

Compound 6 (100 mg) and 0.35 ml of N,N-dimethylethylenediamine were subjected to reaction in the same manner as in Example 7, and the product was treated in the same manner as in Example 8 to obtain 71 mg (51.3%) of the hydrobromide of Compound 10.

m.p. (° C.): 185 to 187

Elementary analysis (%): Calcd. for $C_{19}H_{20}N_4O \cdot HBr \cdot 1.9H_2O$: C, 52.40; H, 5.74; N, 12.86; Found: C, 52.44; H, 5.47; N, 12.82

NMR (DMSO-$d_6$) δ(ppm): 3.13-3.20(2H, m), 3.29(6H, s), 3.52(2H, t, J=6.7 Hz), 5.30(2H, s), 7.61(1H, dt, J=1.3, 7.7 Hz), 7.84(1H, d, J=7.7 Hz), 8.02(1H, dt, J=1.5, 7.8 Hz), 8.30(1H, d, J=7.3 Hz), 8.38(1H, dd, J=1.7, 7.7 Hz), 8.40(1H, d, J=7.0 Hz), 8.71(1H, d, J=7.5 Hz)

IR (KBr) $cm^{-1}$: 1650, 1604, 1513, 1467

EXAMPLE 11

5-Amino-2-methyl-6H-pyrazolo[4,5,1-d,e]acridin-6-one (Compound 11):

3-Methyl-6-nitroindazole (64.5 g), 46.0 g of 2-iodobenzoic acid, 40.8 g of potassium carbonate and 1.89 g of copper(II) oxide were subjected to reaction in the same manner as in Example 1 to obtain 53.6 g (69.4%) of 1-(2-carboxyphenyl)-3-methyl-6-nitroindazole.

The obtained compound was suspended in 565 ml of ethanol, and 2.83 g of 10% palladium-carbon was added thereto, followed by stirring at 50° C. Hydrazine monohydrate (28 ml) was gradually added dropwise to the suspension, and then the mixture was heated under reflux with stirring for 1.5 hours. After cooling, the reaction mixture was filtered through sellaite and the filtrate was concentrated to obtain a crude product of 6-amino-1(2-carboxyphenyl)-3-methylindazole.

To the product was added 1640 g of polyphosphoric acid, and the mixture was stirred at 165° to 175° C. for 6 hours. After cooling, chloroform and water were added to the reaction mixture, and the crystals precipitated were separated by filtration. The extracted chloroform layer was decolored with active charcoal, followed by filtration. The filtrate was dried over anhydrous sodium sulfate and concentrated under reduced pressure. The residue was recrystallized from chloroform-hexane, and the resulting crystals were combined with the previously obtained crystals, whereby 18.8 g (39.6%) of Compound 11 was obtained.

m.p. (° C.): 256 to 258

Elementary analysis (%): Calcd. for $C_{15}H_{11}N_3O$: C, 72.28; H, 4.45; N, 16.86; Found: C, 72.27; H, 4.32; N, 16.95

NMR (CDCl$_3$) δ(ppm): 2.65(3H, s), 6.61(1H, d, J=8.6 Hz), 7.41(1H, dt, J=1.1, 8.2 Hz), 7.68(1H, d, J=8.8 Hz), 7.77(1H, dt, J=1.4, 8.3 Hz), 8.23(1H, d, J=8.3 Hz), 8.45(1H, dd, J=1.2, 8.1 Hz)

IR (KBr) cm$^{-1}$: 3374, 3290, 1644, 1617, 1592, 1574, 1501, 1443

EXAMPLE 12

2-Methyl-5-trifluoroacetylamino-6H-pyrazolo[4,5,1-d,e]acridin-6-one (Compound 12):

Compound 11 (630 mg), 10 ml of trifluoroacetic acid and 5 ml of trifluoroacetic anhydride were stirred at room temperature for 30 minutes. The reaction mixture was concentrated under reduced pressure and chloroform was added to the residue. The solid formed was separated by filtration and washed with chloroform to obtain 818 mg (92.7%) of Compound 12.

m.p. (° C.): >300

Elementary analysis (%): Calcd. for $C_{17}H_{10}F_3N_3O_2.0.2H_2O$: C, 58.53; H, 3.00; N, 12.04; Found: C, 58.57; H, 3.83; N, 11.96

NMR (CDCl$_3$) δ(ppm): 2.81(3H, s), 7.51(1H, dt, J=1.0, 7.7 Hz), 7.91(1H, dt, J=1.6, 7.7 Hz), 8.17(1H, d, J=8.6 Hz), 8.32(1H, dd, J=0.5, 8.3 Hz), 8.52(1H, dd, J=1.2, 8.1 Hz), 8.76(1H, d, J=8.8 Hz)

IR (KBr) cm$^{-1}$: 1729, 1655, 1621, 1567, 1523, 1489, 1470

EXAMPLE 13

5-Acetylamino-2-methyl-6H-pyrazolo[4,5,1-d,e]acridin-6-one (Compound 13):

Compound 11 (630 mg) was dissolved in 50 ml of chloroform, and 0.36 ml of acetyl chloride and then 0.70 ml of triethylamine were added thereto, followed by stirring at room temperature for 16 hours. To the mixture were further added 1.44 ml of acetyl chloride and 2.8 ml of triethylamine, followed by stirring for 6 hours. The reaction mixture was concentrated under reduced pressure, and the residue was extracted with chloroform and water. The resulting chloroform later was dried over anhydrous sodium sulfate and concentrated under reduced pressure. The residue was subjected the silica gel column chromatography with chloroform-acetone (20:1) as the eluent and then recrystallized from chloroform-isopropanol to obtain 337 mg (43.7%) of Compound 13.

m.p. (° C.): 245 to 247

Elementary analysis (%):

Calcd. for $C_{17}H_{13}N_2O_2.0.1H_2O.0.1(CH_3)_2CHOH$: C, 69.28; H, 4.88; N, 13.77; Found: C, 69.15; H 4.44; N, 13.39

NMR (CDCl$_3$) δ(ppm): 2.39(3H, s), 2.71(3H, s), 7.44(1H, dt, J=0.7, 8.1 Hz), 7.82(1H, dt, J=1.5, 8.5 Hz), 7.97(1H, d, J=8.8 Hz), 8.21(1H, d, J=8.6 Hz), 8.41 (1H, dd, J=1.5, 8.1 Hz), 8.74(1H, dt, J=0.5, 8.8 Hz)

IR (KBr) cm$^{-1}$: 1702, 1646, 1612, 1541, 1518, 1490, 1471

EXAMPLE 14

2-Bromomethyl-5-trifluoroacetylamino-6H-pyrazolo[4,5,1-d,e]acridin-6-one (Compound 14):

Compound 12 (877 mg), 452 mg of N-bromosuccinimide and 31 mg of benzoyl peroxide were heated under reflux in 700 ml of carbon tetrachloride with stirring for 16 hours. The reaction mixture was concentrated to about 70 ml under reduced pressure. The crystals precipitated were separated by filtration and recrystallized three times from chloroform to obtain 590 mg (54.8%) of Compound 14.

m.p. (° C.): 292 to 293

Elementary analysis (%):

Calcd. for $C_{17}H_9BrF_3N_3O_2$: C, 48.14; H, 2.14; N, 9.91; Found: C, 48.60; H; 2.05; N, 10.27

NMR (CDCl$_3$) δ(ppm) 4.95(2H, s), 7.55(1H, dt, J=1.1, 8.2 Hz), 7.92(1H, dt, J=1.4, 8.5 Hz), 8.32(1H, dd, J=1.1, 8.3 Hz), 8.35(1H, d, J=8.5 Hz), 8.53(1H, dd, J=1.1, 8.2 Hz), 8.84(1H, d, J=8.5 Hz), 13.24(1H, s)

IR (KBr) cm$^{-1}$: 1730, 1655, 1617, 1550, 1520

EXAMPLE 15

5-Amino-2-(2-aminoethyl]aminomethyl-6H-pyrazolo[4,5,1-d,e]acridin-6-one (Compound 15):

Compound 14 (157 mg) was dissolved in 70 ml of chloroform under heating. After cooling, 1.0 ml of ethylenediamine was added to the solution at room temperature and the mixture was stirred overnight. The reaction mixture was concentrated under reduced pressure, and the residue was dissolved in methanol. An ether solution containing hydrogen chloride was added thereto, and the crystals precipitated were separated by filtration and then dissolved in a solvent mixture of water, methanol and dimethylformamide. The solution was decolored with active charcoal and filtered. The resulting filtrate was concentrated to about 2 ml under reduced pressure and then crystallized from ethanol, whereby 106 mg (67.5%) of the hydrochloride of Compound 15 was obtained.

m.p. (° C.): 290 to 293

Elementary analysis (%) Calcd. for $C_{17}H_{17}N_5O.HCl.0.4H_2O$: C, 48.16; H, 4.94; N, 16.52; Found: C, 48.11; H, 4.78; N, 16.47

NMR (DMSO-d$_6$) δ(ppm): 3.27-3.44(4H, m), 4.75(2H, s), 6.94(1H, d, J=8.8 Hz), 7.58(1H, dt, J=1.0, 8.1 Hz), 7.96(1H, dt, J=1.4, 7.7 Hz), 8.19(1H, d, J=8.0 Hz), 8.27(1H, d, J=7.8 Hz), 8.39(1H, dt, J=1.0, 8.1 Hz)

IR (KBr) cm$^{-1}$: 3376, 1652, 1617, 1591, 1506, 1432

EXAMPLE 16

5-Amino-2-[2-(2-hydroxyethylamino)ethyl-]aminomethyl-6H-[4,5,1-d,e]acridin-6-one (Compound 16):

Compound 14 (50 mg) was dissolved in 20 ml of chloroform under heating. After cooling, 0.2 ml of 2-(2-hydroxyethylamino)ethylamine was added to the solution at room temperature and the mixture was stirred overnight. A small amount of 25% hydrobromic acid-/acetic acid solution was added to the reaction mixture, whereby an oily substance separated. The supernatant was removed by decantation, and ether was added to the remaining oily substance for crystallization. The resulting crystals were recrystallized from methanol-chloroform, followed by further recrystallization from methanol to obtain 11 mg (19.7%) of the hydrobromide of Compound 16.

Elementary analysis (%): Calcd. for $C_{19}H_{21}N_5O_2 \cdot HBr \cdot 0.4CH_3CO_2H \cdot H_2O$: C, 50.14; H, 5.44; N, 14.76; Found: C, 50.05; H, 5.13; N, 14.78

NMR (DMSO-$d_6$) δ(ppm): 3.08–3.72(6H, m), 3.89(2H, m), 4.74(2H, s); 6.95(1H, d, J=8.8 Hz), 7.58(1H, d, J=7.8 Hz), 7.95(1H, dt, J=1.4, 7.8 Hz), 8.19(1H, d, J=8.8 Hz), 8.31(1H, d, J=7.8 Hz), 8.39(1H, d, J=7.8 Hz)

IR (KBr) cm$^{-1}$: 3382, 1656, 1618, 1593, 1503

EXAMPLE 17

5-Amino-2-(2-morpholinoethyl)aminomethyl-6H-[4,5,1-d,e]-acridin-6-one (Compound 17):

Compound 14 (30 mg) was dissolved in 20 ml of chloroform under heating. After cooling, 0.2 ml of 4-(2-aminoethyl)morpholine was added to the solution at room temperature and the mixture was stirred overnight. After the reaction, 1 ml of 25% hydrobromic acid/acetic acid solution was added to the reaction mixture and the solid precipitated was separated by filtration. The resulting filtrate was concentrated under reduced pressure, and the residue was dissolved in methanol. Ether was added to the solution for crystallization to form 12 mg (21.0%) of the hydrobromide of Compound 17.

Elementary analysis (%): Calcd. for $C_{21}H_{23}N_5O_2 \cdot HBr \cdot 1.5H_2O$: C, 51.97; H, 5.61; N, 14.43; Found: C, 52.21; H, 5.75; N, 14.63

NMR (DMSO-$d_6$) δ(ppm): 3.03–4.07(12H, m), 4.74(2H, s), 6.94(1H, d, J=9.0 Hz), 7.58(1H, dt, J=1.1, 8.2 Hz), 7.96(1H, dt, J=1.4, 7.8 Hz), 8.19(1H, d, J=9.0 Hz), 8.27(1H, d, J=7.8 Hz), 8.39(1H, dd, J=1.2, 8.1 Hz)

IR (KBr) cm$^{-1}$: 3390, 1652, 1616, 1592, 1505

EXAMPLE 18

5-Amino-2-(2-dimethylaminoethyl)aminomethyl-6H-pyrazolo[4,5,1-d,e]acridin-6-one (Compound 18):

Compound 14 (40 mg) was dissolved in 15 ml of chloroform under heating. After cooling, 0.2 ml of 2-dimethylaminoethylamine was added to the solution at room temperature and the mixture was stirred overnight. The reaction mixture was then treated in the same manner as in Example 17 to obtain 30 mg (68.1%) of the hydrobromide of Compound 18.

m.p. (° C.): 200 to 202

Elementary analysis (%): Calcd. for $C_{19}H_{21}N_5O \cdot 0.4HBr \cdot 0.6CH_3CO_2H \cdot 1.8H_2O$: C, 51.77; H, 5.51; N, 14.94; Found: C, 51.61; H, 4.88; N, 14.98

NMR (DMSO-$d_6$) δ(ppm): 3.26(6H, s), 3.26–3.33(2H, m), 3.63(2H, t, J=7.0 Hz), 5.14(2H, s), 7.01(1H, d, J=9.0 Hz), 7.66(1H, dt, J=1.0, 7.9 Hz), 7.96(1H, dt, J=1.3, 7.7 Hz), 8.20(1H, d, J=9.0 Hz), 8.32(1H, d, J=7.9 Hz), 8.40(1H, dd, J=1.1, 8.1 Hz)

IR (KBr) cm$^{-1}$: 3376, 1656, 1617, 1595, 1573, 1506, 1426

EXAMPLE 19

5-(2-Hydroxyethyl)amino-2-methyl-6H-pyrazolo[4,5,1-d,e]acridin-6-one (Compound 19):

Compound 11 (100 mg) and 5 ml of ethylene oxide were stirred in 5 ml of acetic acid and 5 ml of water at room temperature for 7 days. To the mixture were further added 2 ml of ethylene oxide, 2 ml of acetic acid and 2 ml of water, followed by stirring for 11 days. The crystals precipitated were separated by filtration and recrystallized from chloroform-carbon tetrachloride to obtain 30 mg (25.6%) of Compound 19.

m.p. (° C.): 240 to 242

Elementary analysis: (%): Calcd. for $C_{17}H_{15}N_3O_2 \cdot 0.2H_2O$: C, 68.77; H, 5.23; N, 14.15; Found: C, 68.69; H, 4.96; N, 13.75

NMR (DMSO-$d_6$) δ(ppm): 2.61(3H, s), 3.53(2H, q, J=5.4 Hz), 3.72(2H, t, J=5.4 Hz), 6.88(1H, d, J=9.0 Hz), 7.49(1H, dt, J=1.0, 7.7 Hz), 7.88(1H, dt, J=1.5, 7.8 Hz), 8.00(1H, d, J=8.8 Hz), 8.17(1H, d, J=7.6 Hz), 8.35(1H, dd, J=1.5, 8.1 Hz)

IR (KBr) cm$^{-1}$: 3434, 1652, 1615, 1597, 1570, 1521

EXAMPLE 20

5-Bromo-2-bromomethyl-6H-pyrazolo[4,5,1-d,e]acridin-6-one (Compound 20):

A solution of 0.38 g of sodium nitrite in 4 ml of sulfuric acid was cooled, and 10 ml of acetic acid and then 1.27 g of Compound 11 were added thereto. After the temperature of the mixture was raised to room temperature, the mixture was stirred for 30 minutes. Then, 1.60 g of copper (I) bromide and 10 ml of concentrated hydrobromic acid were added thereto, followed by stirring at 80° C. for 20 minutes. To the reaction mixture was added 30 ml of water, and after cooling, the solid precipitated was separated by filtration. The solid was heated under reflux in 300 ml of chloroform, and the insoluble substance was filtered off. The chloroform layer was washed with water, dried over anhydrous sodium sulfate and concentrated under reduced pressure. The resulting residue was crystallized from isopropylether to obtain 1.39 g (87.0%) of 5-bromo-2-methyl-6H-pyrazolo[4,5,1-d,e]acridin-6-one.

The obtained compound (1.00 g) was treated in the same manner as in Example 6 to obtain 0.71 g (56.3%) of Compound 20.

m.p. (° C.): 204 to 205

Elementary analysis (%): Calcd. for $C_{15}H_8Br_2N_2O$: C, 45.95; H, 2.06; N, 7.15; Found: C, 46.06; H, 2.03; N, 6.98

NMR (CDCl$_3$) δ(ppm): 4.93(2H, s), 7.48(1H, dt, J=1.1, 8.1 Hz), 7.81(1H, d, J=8.4 Hz), 7.83(1H, dt, J=1.5, 8.2 Hz), 8.05(1H, d, J=8.4 Hz), 8.22(1H, dd, J=1.1, 8.2 Hz), 8.50(1H, dd, J=1.5, 8.1 Hz)

IR (KBr) cm$^{-1}$: 1649, 1614, 1603, 1587, 1514, 1480

EXAMPLE 21

5-(2-Aminoethyl)amino-2-(2-aminoethyl)aminomethyl-6H-pyrazolo[4,5,1-d,e]acridin-6-one (Compound 21):

Compound 20 (100 mg) was dissolved in 5 ml of chloroform, and 2 ml of ethylenediamine was added to the solution. The mixture was heated under reflux with stirring for 1.5 hours. After the reaction, the reaction mixture was concentrated under reduced pressure and the resulting residue was dissolved in methanol. To the solution was added isopropanol containing hydrogen chloride to precipitate crystals. The crystals were separated by filtration and recrystallized from water-methanol to obtain 51 mg (40.8%) of the hydrochloride of Compound 21.

m.p. (°C): 304 to 306

Elementary analysis (%): Calcd. for $C_{19}H_{22}N_6O \cdot 3.8HCl$: C, 46.67; H, 5.32; N, 17.8; Found: C, 46.74; H, 5.20; N, 16.77

NMR (DMSO-$d_6$) $\delta$(ppm): 3.10–3.48(6H, m), 3.87(2H, q, J=6.2 Hz), 4.77(2H, s), 7.22(1H, d, J=9.0 Hz), 7.60 (1H, dt, J=0.9, 7.7 Hz), 7.98(1H, dt, J=1.3, 4.7 Hz), 8.29(1H, d, J=8.1 Hz), 8.41(1H, dd, J=1.2, 7.6 Hz), 8.44(1H, d, J=8.8 Hz)

IR (KBr) cm$^{-1}$: 1652, 1615, 1594, 1567, 1518

EXAMPLE 22

5-(3-Aminopropyl)amino-2-(3-aminopropyl)aminomethyl-6H-pyrazolo[4,5,1-d,e]acridin-6-one (Compound 22):

Compound 20 (100 mg) and 2 ml of 1,3-propanediamine were subjected to reaction in the same manner as in Example 21 to obtain 110 mg (83.4%) of the hydrochloride of Compound 22.

m.p. (°C): 282 to 285

Elementary analysis (%): Calcd. for $C_{21}H_{26}N_6O \cdot 3.8HCl$: C, 48.78; H, 5.81; N, 16.25; Found: C, 48.88; H, 5.69; N, 16.26

NMR (DMSO-$d_6$) $\delta$(ppm): 2.02(2H, quint. J=7.3 Hz), 2.10 (2H, quint. J=7.6 Hz), 2.91–2.95(4H, m), 3.21(2H, m), 3.68(2H, q, J=6.5 Hz), 4.66(2H, s), 7.11(1H, d, J=9.3 Hz), 7.59(1H, dt, J=1.0, 7.7 Hz), 7.96 (1H, dt, J=1.3, 7.7 Hz), 8.27(1H, dt, J=8.3 Hz), 8.40(1H, dd, J=1.2, 8.1 Hz), 8.43(1H, d, J=9.3 Hz)

IR (KBr) cm$^{-1}$: 3405, 1651, 1614, 1595, 1568, 1515, 1456

EXAMPLE 23

5-(2-Dimethylaminoethyl)amino-2-(2-dimethylaminoethyl)aminomethyl-6H-pyrazolo[4,5,1-d,e]acridin-6-one (Compound 23):

Compound 20 (90 mg) and 3 ml of N,N-dimethylethylenediamine were subjected to reaction in the same manner as in Example 21 to obtain 79 mg (57.0%) of the hydrochloride of Compound 23.

m.p. (°C): 250 to 251

Elementary analysis (%): Calcd. for $C_{23}H_{30}N_6O \cdot 5.3HCl \cdot 0.2H_2O$: C, 45.78; H, 5.96; N, 13.93; Found: C, 45.80; H, 5.76; N;13 80

NMR (DMSO-$d_6$) $\delta$(ppm): 2.88(12H, s), 3.23–3.66(6H, m), 4.01(2H, q, J=5.6 Hz), 4.80(2H, s), 7.25(11H, d, J=9.0 Hz), 7.61(1H, t, J=7.7 Hz), 7.99(1H, dt, J=1.3, 7.8 Hz), 8.29(1H, d, J=8.3 Hz), 8.41(1H, d, J=7.8 Hz), 8.44(1H, d, J=8.8 Hz)

IR (KBr) cm$^{-1}$: 1650, 1616, 1598, 1568, 1519, 1456

EXAMPLE 24

5-Bromo-2-bromomethyl-7-methoxy-6H-pyrazolo[4,5,1-d,e]acridin-6-one (Compound 24):

3-Methyl-6-nitroindazole (5.31 g) and 6.93 g of 2-bromo-6-methoxybenzoic acid were subjected to reaction in the same manner as in Example 11 to obtain 1-(2-carboxy-3-methoxyphenyl)-3-methyl-6-nitroindazole (yield: 75.9%). The nitro group of the compound was reduced to give 6-amino-(2-carboxy-3-methoxyphenyl)-3-methylindazole (yield: 100%), which was then cyclized to obtain 1.83 g (28.9%) of 5-amino-7-methoxy-2-methyl-6H-pyrazolo[4,5,1-d,e]acridin-6-one.

The obtained compound (1.67 g) was treated in the same manner as in Example 20 to obtain 1.26 g (58.4%) of Compound 24 through 5-bromo-7-methoxy-2-methyl-6H-pyrazolo[4,5,1-d,e]acridin-6-one (yield: 83.9%).

m.p. (°C): 251 to 252

Elementary analysis (%): Calcd. for $C_{16}H_{10}Br_2N_2O_2$: C, 45.53; H, 2.39; N, 6.64; Found: C, 45.59; H, 2.32; N, 6.49

NMR (DMSO-$d_6$) $\delta$(ppm): 3.95(3H, s), 5.22(2H, s), 7.12 (1H, dd, J=1.1, 8.3 Hz), 7.74(1H, dd, J=1.2, 8.2 Hz), 7.82(1H, t, J=8.2 Hz), 7.84(1H, d, J=8.2 Hz), 8.21(1H, d, J=8.2 Hz)

IR (KBr) cm$^{-1}$: 1657, 1624, 1602, 1516, 1479

EXAMPLE 25

5-(2-Aminoethyl)amino-2-(2-aminoethyl)aminomethyl-7-methoxy-6H-pyrazolo[4,5,1-d,e]acridin-6-one (Compound 25):

Compound 24 (100 mg) and 2 ml of ethylenediamine were heated under reflux in 10 ml of chloroform with stirring for one hour. Then, 10 ml of methanol was added and the mixture was heated under reflux for one hour. After the reaction, the reaction mixture was concentrated under reduced pressure and the resulting residue was dissolved in 20 ml of methanol under heating, followed by addition of isopropanol containing hydrogen chloride. The resulting solution was concentrated under reduced pressure to about a half of its volume and then cooled. The crystals precipitated were separated by filtration and recrystallized from water-methanol-ethanol to obtain 100 mg (79.2%) of the hydrochloride of Compound 25.

m.p. (°C): 254 to 256

Elementary analysis (%): Calcd. for $C_{20}H_{24}N_6O_2 \cdot 3.2HCl \cdot 2H_2O$: C, 45.06; H, 5.90; N, 15.76; Found: C, 45.05; H, 5.82; N, 15.58

NMR (DMSO-$d_6$) $\delta$(ppm): 3.12(2H, m), 3.30–3.48(4H, m), 3.83(2H, q, J=6.3 Hz), 3.93(3H, s), 4.72(2H, s), 7.09(1H, dd, J=1.2, 5.6 Hz), 7.12(1H, d, J=9.3 Hz), 7.81–7.83(2H, m), 8.29(1H, d, J=9.0 Hz)

IR (KBr) cm$^{-1}$: 3420, 1657, 1597, 1570, 1521, 1484

EXAMPLE 26

5-(3-Aminopropyl)amino-2-(3-aminopropyl)aminomethyl-7-methoxy-6H-pyrazolo[4,5,1-d,e]acridin-6-one (Compound 26):

Compound 24 (100 mg) and 2 ml of 1,3-propanediamine were subjected to reaction in the same manner as in Example 25 to obtain 111 mg (84.1%) of the hydrochloride of Compound 26.

m.p. (°C): 253 to 256

Elementary analysis (%): Calcd. for $C_{22}H_{28}N_6O_2 \cdot 3.6HCl \cdot 1.2H_2O$ C, 47.37; H, 6.07; N, 15.07; Found: C, 47.55; H, 5.87; N, 14.42

NMR (DMSO-$d_6$) $\delta$(ppm): 1.95–2.15(4H, m), 2.90–2.96(4H, m), 3.21(2H, m), 3.62(2H, q, J=5.9 Hz), 3.94(3H, s), 4.63(2H, s), 7.04(1H, d, J=9.3 Hz), 7.11(1H, dd, J=2.7, 6.6 Hz), 7.80–7.87(2H, m), 8.32(1H, d, J=9.0 Hz)

IR (KBr) cm$^{-1}$: 3415, 1656, 1597, 1569, 1520

EXAMPLE 27

5-(2-Dimethylaminoethyl)amino-2-(2-dimethylaminoethyl)aminomethyl-7-methoxy-6H-pyrazolo[4,5,1-d,e]acridin-6-one (Compound 27):

Compound 24 (150 mg) and 3 ml of N,N-dimethylethylenediamine were subjected to reaction in the same manner as in Example 25 to obtain 82 mg (37.6%) of the hydrochloride of Compound 27.

m.p. (° C.): 229 to 230

Elementary analysis (%): Calcd. for $C_{24}H_{32}N_6O_2 \cdot 4.4HCl \cdot H_2O$: C, 46.87; H, 6.29; N, 13.67; Found: C, 46.85; H, 6.26; N, 13.53

NMR (DMSO-d6) δ(ppm): 2.86(6H, s), 3.32(6H, s), 3.32-3.49(4H, m), 3.82-3.87(2H, m), 3.95(3H, s), 3.95-3.99 (2H, m), 5.23(2H, s), 7.15(1H, dd, J=1.1, 8.2 Hz), 7.28(1H, d, J=9.0 Hz), 7.85(1H, t, J=8.2 Hz), 7.94(1H, dd, J=1.1, 8.2 Hz), 8.38(1H, d, J=8.8 Hz)

IR (KBr) cm$^{-1}$: 1656, 1599, 1569, 1515, 1464

EXAMPLE 28

5-(2-Aminoethyl)amino-2-(2-aminoethyl)aminomethyl-7-hydroxy-6H-pyrazolo[4,5,1-d,e]acridin-6-one (Compound 28):

The hydrochloride of Compound 25 (92 mg) was heated under reflux in 1.8 ml of concentrated hydrochloric acid with stirring for 11 hours. The reaction mixture was concentrated under reduced pressure, and the crystals formed as a residue were recrystallized from water-methanol-ethanol to obtain 85 mg (96.5%) of the hydrochloride of Compound 28.

m.p. (° C.): 251 to 253

Elementary analysis (%): Calcd. for $C_{19}H_{22}N_6O_2 \cdot 3.3HCl \cdot 1.3H_2O$: C, 44.73; H, 5.51; N, 16.47; Found: C, 44.78; H, 5.42; N, 16.19

NMR (DMSO-d6) δ(ppm): 3.10(2H, m), 3.28-3.47(4H, m), 3.88(2H, q, J=6.1 Hz), 4.76(2H, s), 6.89(1H, dd, J=7.9 Hz), 7.22(1H, d, J=9.5 Hz), 7.67(1H, dd, J=0.9, 8.2 Hz), 7.81(1H, t, J=8.2 Hz), 8.45(1H, d, J=9.2 Hz) 13.71(1H s)

IR (KBr) cm$^{-1}$: 3415, 1659, 1594, 1515, 1462

EXAMPLE 29

5-(3-Aminopropyl)amino-2-(3-aminopropyl)aminomethyl-7-hydroxy-6H-pyrazolo[4,5,1-d,e]acridin-6-one (Compound 29):

From 170 mg of the hydrochloride of Compound 26 was obtained 136 mg (84.1%) of the hydrochloride of Compound in the same manner as in Example 28.

m.p. (° C.): 291 to 292

Elementary analysis (%): Calcd. for $C_{21}H_{26}N_6O_2 \cdot 2.8HCl \cdot 1.9H_2O$: C, 47.52; H, 6.19; N, 15.83; Found: C, 47.53; H, 5.98; N, 15.67

NMR (DMSO-d6) δ(ppm): 1.99(2H, q. J=7.1 Hz), 2.12 (2H, quint. J=7.6 Hz), 2.90-2.96(4H, m), 3.17-3.22 (2H, m), 3.69(2H, q, J=6.6 Hz), 4.65(2H, s), 6.88 (1H, dd, J=0.9, 8.2 Hz), 7.12(1H, d, J=9.2 Hz), 7.65(1H, dd, J=0.9, 8.2 Hz), 7.80(1H, t, J=8.1 Hz), 8.45(1H, d, J=9.2 Hz), 13.70(1H, s)

IR (KBr) cm$^{-1}$: 3420, 1657, 1593, 1575, 1515, 1470

EXAMPLE 30

5-(2-Dimethylaminoethyl)amino-2-(2-dimethylaminoethyl)aminomethyl-7-hydroxy-6H-pyrazolo[4,5,1-d,e]acridin-6-one (Compound 30):

From 68 mg of the hydrochloride of Compound 27 was obtained 61 mg (90.7%) of the hydrochloride of Compound 30 in the same manner as in Example 28.

m.p. (° C.): 210 to 211

Elementary analysis (%): Calcd. for $C_{23}H_{30}N_6O_2 \cdot 4.6HCl \cdot 0.9H_2O$: C, 45.55; H, 6.05; N, 13.86; Found: C, 45.51; H, 6.05; N, 13.76

NMR (DMSO-d6) δ(ppm): 2.86(6H, s), 3.32(6H, s), 3.32-3.49(4H, m), 3.83-3.85(2H, m), 4.06(2H, q, J=6.4 Hz), 5.27(2H, s), 6.96(1H, dd, J=1.1, 8.1 Hz), 7.36(1H, d, J=9.2 Hz), 7.74(1H, dd, J=1.2, 8.2 Hz), 7.82(1H, t, J=8.1 Hz), 8.52(1H, d, J=8.9 Hz), 13.63 (1H, s)

IR (KBr) cm$^{-1}$: 1658, 1596, 1574, 1513, 1470

EXAMPLE 31

2-(2-Dimethylaminoethyloxy)carbonyl-6H-pyrazolo[4,5,1-d,e]acridin-6-one (Compound 31):

Compound 1 (132 mg) and 0.061 ml of 2-dimethylaminoethanol were subjected to reaction in the same manner as in Example 3 to obtain 159 mg (94.9%) of Compound 31. The compound was converted into its hydrochloride in a conventional manner.

m.p. (° C.): 256 to 258

Elementary analysis (%): Calcd. for $C_{19}H_{17}N_3O_3 \cdot HCl \cdot H_2O$: C, 58.54; H, 5.17; N, 10.78; Found: C, 58.37; H, 4.88; N, 10.86

NMR (D₂O) δ(ppm): 3.11(6H, s), 3.74(2H, t, J=4.9 Hz), 4.75(2H, t, J=4.9 Hz), 6.86(1H, d, J=8.1 Hz), 7.07 (1H, t, J=7.7 Hz), 7.20(1H, dt, J=0.8, 8.1 Hz), 7.31 (1H, d, J=7.3 Hz), 7.43(1H, dt, J=1.4, 8.1 Hz), 7.47 (1H, dd, J=0.9, 8.1 Hz), 7.59(1H, d, J=7.7 Hz)

IR (KBr) cm$^{-1}$: 1724, 1652, 1603, 1506, 1469, 1423

EXAMPLE 32

5-(3-Methylaminopropyl)amino-2-(3-methylaminopropyl)aminomethyl-6H-pyrazolo[4,5,1-d,e]acridin-6-one (Compound 32):

Compound 20 (260 mg) was dissolved in 20 ml of dioxane, and 2.93 g of N-benzyloxycarbonyl-N-methyl-1,3-propanediamine was added to the solution. The mixture was heated under reflux with stirring for 7.5 hours. After the reaction, the reaction mixture was concentrated under reduced pressure and the resulting residue was subjected to silica gel column chromatography with chloroform-methanol (30:1) as the eluent to obtain 270 mg (75.4%) of 5-[3-(N-benzyloxycarbonyl-N-methyl)aminopropyl]amino-2-[3-(N-benzyloxycarbonyl-N-methyl)aminopropyl]aminomethyl-6H-pyrazolo[4,5,1-d,e]acridin-6-one.

To 270 mg of the obtained compound was added 5 ml of 25% hydrobromic acid/acetic acid solution, followed by stirring at room temperature for one hour. The reaction mixture was concentrated under reduced pressure, and the residue was recrystallized from water-methanol-ethanol to obtain 215 mg (60.2%) cf the hydrobromide of Compound 32.

m.p. (° C.): 241 to 242

Elementary analysis (%): Calcd. for $C_{23}H_{30}N_6O \cdot 3.4HBr \cdot 0.6CH_3CO_2H$: C, 40.50; H, 5.03; N, 11.71; Found: C, 40.59; H, 5.13; N, 11.70

NMR (DMSO-d₆) δ(ppm): 2.07(4H, m), 2.69(6H, d, J=5.6 Hz), 3.04(4H, m), 3.25(2H, t, J=7.3 Hz), 3.68(2H, q, J=6.6 Hz), 4.76(2H, s), 7.15(1H, d, J=9.3 Hz), 7.61(1H, dt, J=1.1, 7.6 Hz), 7.99(1H, dt, J=0.9, 7.2 Hz), 8.29(1H, d, J=9.7 Hz), 8.36(1H, d, J=9.0 Hz), 8.42(1H, dd, J=1.2, 8.1 Hz)

IR (KBr) cm$^{-1}$: 3412, 1654, 1595, 1570, 1458

EXAMPLE 33

5-(2-Methylaminoethyl)amino-2-(2-methylaminoethyl)aminomethyl-6H-pyrazolo[4,5,1-d,e]acridin-6-one (Compound 33):

Compound 20 (300 mg) and 769 mg of N-benzyloxycarbonyl-N-methylethylenediamine were subjected to reaction in the same manner as in Example 32 to obtain 109 mg (32.7%) of 5-[2-(N-benzyloxycarbonyl-N-methyl)aminoethyl]amino-2-(N-benzyloxycarbonyl-N-methyl)aminoethyl]aminomethyl-6H-pyrazolo[4,5,1-d,e]acridin-6-one.

From 31 mg of this compound was obtained 19 mg (57.5%) of the hydrobromide of Compound 33 in the same manner as in Example 32.

m.p. (° C.): 266 to 267

Elementary analysis (%): Calcd. for $C_{21}H_{26}N_6O \cdot 3.4HBr \cdot 0.6CH_3CO_2H$: C, 40.05; H, 4.90; N, 12.18; Found: C, 40.20; H, 5.19; N, 11.81

NMR (DMSO-d$_6$) δ(ppm): 2.66(6H, d, J=5.9 Hz), 3.26(2H, t, J=5.6 Hz), 3.39(2H, t, J=6.7 Hz), 3.56(2H, t, J=6.5 Hz), 3.92(2H, q, J=6.3 Hz), 4.86(2H, s), 7.24 (1H, d, J=9.3 Hz), 7.62(1H, dt, J=1.0, 7.6 Hz), 8.00(1H, dt, J=1.0, 8.3 Hz), 8.30(1H, d, J=8.1 Hz), 8.39(1H, d, J=9.3 Hz), 8.43(1H, dd, J=1.2, 8.3 Hz)

IR (KBr) cm$^{-1}$: 1650, 1614, 1593, 1567, 1514, 1418

EXAMPLE 34

5-(2-Ethylaminoethyl)amino-2-(2-ethylaminoethyl)aminomethyl-6H-pyrazolo[4,5,1-d,e]acridin-6-one (Compound 34):

Compound 20 (250 mg) and 1.4 g of N-benzyloxycarbonyl-N-ethylethylenediamine were subjected to reaction in the same manner as in Example 32 to obtain 273 mg (65.6%) (N-benzyloxycarbonyl-N-ethyl)aminoethyl]aminomethyl-6H-pyrazolo[4,5,1-d,e]acridin-6-one.

The obtained compound was treated in the same manner as in Example 32 to obtain 150 mg (52.6%) of the hydrobromide of Compound 34.

m.p. (° C.): 196 to 198

Elementary analysis (%): Calcd. for $C_{23}H_{30}N_6O \cdot 3.4HBr$: C, 40.05; H, 4.90; N, 12.18; Found: C, 40.20; H, 5.19; N, 11.81

NMR (DMSO-d$_6$) δ(ppm): 1.22(3H, t, J=7.2 Hz), 1.24(3H, t, J=7.2 Hz), 3.06(2H, q, J=7.1 Hz), 3.07(2H, q, J=7.3 Hz), 3.25(2H, m), 3.39(2H, t, J=6.5 Hz), 3.55 (2H, t, J=6.3 Hz), 3.92(2H, q, J=6.2 Hz), 4.86(2H, s), 7.25(1H, d, J=9.0 Hz), 7.62(1H, dt, J=0.9, 7.6 Hz), 8.00(1H, dt, J=1.2, 7.8 Hz), 8.30(1H, d, J=8.3 Hz), 8.39(1H, d, J=9.3 Hz), 8.43(1H, dd, J=1.3, 8.2 Hz)

IR (KBr) cm$^{-1}$: 1651, 1615, 1595, 1515, 1436

EXAMPLE 35

5-(2-Morpholinoethyl)amino-2-(2-morpholinoethyl)aminomethyl-6H-pyrazolo[4,5,1-d,e]acridin-6-one (Compound 35):

Compound 20 (250 mg) and 2 ml of N-(2-aminoethyl)morpholine were subjected to reaction in the same manner as in Example 21 to obtain 261 mg (43.5%) of the hydrochloride of Compound 35.

m.p. (° C.): 253 to 254

Elementary analysis (%): Calcd. for $C_{27}H_{34}N_6O_3 \cdot 3.6HCl \cdot 2H_2O$: C, 48.89; H, 6.41; N, 12.67; Found: C, 48.95; H, 6.30; N, 12.29

NMR (DMSO-d$_6$) δ(ppm): 3.22–4.10(24H, m), 4.78(2H, s), 7.26(1H, d, J=9.0 Hz), 7.59(1H, dt, J=0.9, 7.6 Hz), 7.69(1H, dt, J=1.3, 7.7 Hz), 8.27(1H, d, J=8.1 Hz), 8.39(1H, dt, J=1.2, 8.1 Hz), 8.44(1H, d, J=8.8 Hz)

IR (KBr) cm$^{-1}$: 1652, 1615, 1598, 1568, 1520, 1436

EXAMPLE 36

5-(2-Diethylaminoethyl)amino-2-(2-diethylaminoethyl)aminomethyl-6H-pyrazolo[4,5,1-d,e]acridin-6-one (Compound 36):

Compound 20 (257 mg) and 2 ml of N,N-diethylethylenediamine were subjected to reaction in the same manner as in Example 21 to obtain 276 mg (67.4%) of the hydrochloride of Compound 36.

m.p. (° C.): 266 to 267

Elementary analysis (%): Calcd. for $C_{27}H_{38}N_6O \cdot 3.9HCl \cdot H_2O$: C, 52.07; H, 7.10; N, 13.49; Found: C, 52.03; H, 7.04; N, 13.42

NMR (DMSO-d$_6$) δ(ppm): 1.27(6H, t, J=7.4 Hz), 1.29(6H, t, J=7.3 Hz), 3.24(8H, m), 3.37(2H, t, J=6.7 Hz), 3.58(2H, t, J=6.5 Hz), 3.69(2H, t, J=6.7 Hz), 4.04 (2H, t, J=7.1 Hz), 4.77(2H, s), 7.28(1H, d, J=9.3 Hz), 7.59(1H, dt, J=0.9, 7.2 Hz), 7.97(1H, dt, J=1.4, 7.8 Hz), 8.26(1H, d, J=8.3 Hz), 8.39(1H, dd, J=1.4, 7.8 Hz), 8.46(1H, d, J=8.8 Hz)

IR (KBr) cm$^{-1}$: 1651, 1617, 1596, 1568, 1520, 1430

EXAMPLE 37

5-(4-Aminobutyl)amino-2-(4-aminobutyl)aminomethyl-6H-pyrazolo[4,5,1-d,e]acridin-6-one (Compound 37):

Compound 20 (250 mg) was dissolved in 20 ml of dioxane, and 0.9 g of 1,4-butanediamine was added to the solution. The mixture was heated under reflux with stirring for one hour. The reaction mixture was then concentrated and the resulting residue was dissolved in 5 ml of 2N aqueous sodium hydroxide solution. To the solution were added 5 ml of diethylether and 4 ml of benzyloxycarbonyl chloride, followed by stirring at room temperature for 18 hours. The reaction mixture was then extracted with ether, dried over anhydrous sodium sulfate and concentrated under reduced pressure. The resulting residue was subjected to silica gel column chromatography with ethyl acetate-hexane (1:5) as the eluent to obtain 156 mg (36.7%) of 5-(4-benzyloxycarbonylaminobutyl)amino-2-(4-benzyloxycarbonylaminobutyl)aminomethyl-6H-pyrazolo[4,5,1-d,e]acridin-6-one.

The obtained compound (156 mg) was dissolved in 25% hydrobromic acid/acetic acid solution, followed by stirring at room temperature for one hour. The reaction mixture was concentrated under reduced pressure, and the resulting residue was recrystallized from water-methanol-ethanol to obtain 75 mg (45.9%) of Compound 37.

m.p. (° C.): 272 to 274

Elementary analysis (%): Calcd. for $C_{23}H_{30}N_6O \cdot 3.2HBr \cdot 0.7CH_3CO_2H$: C, 41.42; H, 5.21; N, 11.88; Found: C, 41.59; H, 5.35; N, 11.89

NMR (DMSO-d$_6$) δ(ppm): 1.66–1.84(8H, m), 2.88(4H, m), 3.19(2H, m), 3.59(2H, q, J=5.9 Hz), 4.74(2H, s), 7.12(1H, d, J=9.3 Hz), 7.61(1H, dt, J=1.0, 7.7 Hz), 7.99(1H, dt, J=1.3, 7.7 Hz), 8.27(1H, d, J=8.1 Hz), 8.34(1H, d, J=9.0 Hz), 8.41(1H, dd, J=1.2, 8.1 Hz)

IR (KBr) cm$^{-1}$: 3420, 1651, 1615, 1594, 1572, 1519

EXAMPLE 38

2-[N-(2-aminoethyl)-N-methyl]aminomethyl-5-(2-methylaminoethyl)amino-6H-pyrazolo[4,5,1-d,e]acridin-6-one (Compound 38):

Compound 20 (300 mg) and 3 ml of N-methylethylenediamine were subjected to reaction in the same manner as in Example 21 to obtain 83 mg (19.2%) of the hydrochloride of Compound 38.

m.p. (° C.): 256 to 258

Elementary analysis (%): Calcd. for $C_{21}H_{26}N_6O \cdot 4.2HCl \cdot 1.9H_2O$: C, 44.58; H, 6.06; N, 14.85; Found: C, 44.64; H, 5.77; N, 14.66

NMR (DMSO-d$_6$) δ(ppm): 2.61(3H, d, J=4.9 Hz), 2.93(3H, s), 3.21(2H, m), 3.41(2H, m), 3.95(2H, q, J=6.6 Hz), 4.94(2H, s), 7.25(1H, d, J=9.0 Hz), 7.60(1H, dt, J=0.9, 7.8 Hz), 7.96(1H, dt, J=1.3, 7.8 Hz), 8.30(1H, d, J=8.1 Hz), 8.35(1H, dd, J=1.0, 8.1 Hz), 8.45(1H, d, J=8.8 Hz)

IR (KBr) cm$^{-1}$: 3418, 1651, 1615, 1596, 1567, 1514,

EXAMPLE 39

5-(3-Dimethylaminopropyl)amino-2-(3-dimethylaminopropyl)aminomethyl-6H-pyrazolo[4,5,1-d,e]acridin-6-one (Compound 39):

Compound 20 (400 mg) and 4 ml of N,N-dimethyl-1,3-propanediamine were subjected to reaction in the same manner as in Example 21 to obtain 198 mg (32.2%) of the hydrochloride of Compound 39.

m.p (° C.): 241 to 243

Elementary analysis (%): Calcd. for $C_{25}H_{34}N_6O \cdot 3.2HCl \cdot 2.9H_2O$ C, 49.76; H, 7.18; N, 13.93; Found: C, 49.93; H, 6.81; N, 13.36

NMR (DMSO-d$_6$) δ(ppm): 2.78(6H, s), 2.79(6H, s), 2.13 (2H, t, J=7.3 Hz), 2.28(2H, t, J=7.4 Hz), 2.89(2H, m), 3.20(2H, m), 3.66(4H, m), 5.17(2H, s), 7.19 (1H, d, J=9.0 Hz), 7.62(1H, dt, J=0.9, 7.5 Hz), 7.97(1H, dt, J=1.4, 7.8 Hz), 8.30(1H, d, J=8.3 Hz), 8.36(1H, dd, J=1.7, 9.4 Hz), 8.44(1H, d, J=9.0Hz)

IR (KBr cm$^{-1}$: 1651, 1596, 1570, 1479, 1401

EXAMPLE 40

5-Bromo-2-(2-dimethylaminoethyl)aminomethyl-7-methoxy-6H-pyrazolo[4,5,1-d,e]acridin-6-one (Compound 40):

Compound 24 (270 mg) was dissolved in 27 ml of chloroform, and 67 mg of N,N-dimethylethylenediamine was added to the solution. The mixture was stirred at room temperature overnight, and the crystals precipitated were separated by filtration to obtain 272 mg (79.7%) of the hydrobromide of Compound 40.

m.p. (° C.): 222 to 224

Elementary analysis (%): Calcd. for $C_{20}H_{21}BrN_4O_2 \cdot HBr \cdot 1.3H_2O$ C, 45.01; H, 4.64; N, 10.49; Found: C, 45.11; H, 4.23; N, 10.13

NMR (DMSO-d$_6$) δ(ppm): 3.25(6H, s), 3.37(2H, m), 3.50–3.55(2H, m), 3.97(3H, s), 5.23(2H, s), 7.18(1H, dd, J=1.9, 7.6 Hz), 7.84–7.88(2H, m), 7.91(1H, d, J=8 4 Hz), 8.39(1H, d, J=8.4 Hz)

IR (KBr) cm$^{-1}$: 1652, 1622, 1599, 1512, 1471

EXAMPLE 41

2-(2-Dimethylaminoethyl)aminomethyl-5-[2-(2-hydroxyethylamino)ethyl]amino-7-methoxy-6H-pyrazolo[4,5,1-d,e]acridin-6-one (Compound 41):

Compound 40 (220 mg) was dissolved in 10 ml of methanol, and 2 ml of 2-(2-aminoethylamino)ethanol was added to the solution. The mixture was heated under reflux with stirring for one hour. The reaction mixture was then concentrated under reduced pressure, and the resulting residue was crystallized from methanol-isopropanol and separated by filtration. The crystals were dissolved in methanol and isopropanol containing hydrogen chloride was added to the solution, whereby Compound 41 crystallized as the hydrochloride. By recrystallization from methanol-ethanol, 183 mg (71.6%) of the hydrochloride of Compound 41 was obtained.

m.p. (° C.): 232 to 234

Elementary analysis (%): Calcd. for $C_{24}H_{32}N_6O_3 \cdot 3.7HCl \cdot 2H_2O$: C, 46.23; H, 6.41; N, 13.49; Found: C, 46.23; H, 6.39; N, 13.29

NMR (DMSO-d$_6$) (ppm): 3.07(2H, m), 3.24(2H, m), 3.32 (3H, s), 3.43–3.51(2H, m), 3.71(2H, t, J=5.1 Hz), 3.82–3.95(4H, m), 3.95(3H, s), 5.23(2H, s), 7.15 (1H, d, J=7.3 Hz), 7.28(1H, d, J=9.3 Hz), 7.85(1H, t, J=8.3 Hz), 7.93(1H, dd, J=0.9, 8.2 Hz), 8.37(1H, d, J=9.0 Hz)

IR (KBr) cm$^{-1}$: 3400, 1656, 1598, 1567, 1515, 1454

EXAMPLE 42

2-(2-Dimethylaminoethyl)aminomethyl-7-hydroxy-5-[2-(2-hydroxyethylamino)ethylamino-6H-pyrazolo[4,5,1-d,e]acridin-6-one (Compound 42):

Compound 41 (155 mg) and 16 mg of concentrated hydrochloric acid were heated under reflux with stirring for 14 hours. The reaction mixture was concentrated under reduced pressure, and the resulting residue was crystallized from methanol-ethanol. By recrystallization from methanol-ethanol, 94 mg (64.4%) of the hydrochloride of Compound 42 was obtained.

m.p. (° C.): 240 to 241

Elementary analysis (%): Calcd. for $C_{23}H_{30}N_6O_3 \cdot 4.2HCl \cdot 0.4H_2O$: C, 46.12; H, 5.89; N, 14.03; Found: C, 46.27; H, 5.89; N, 13.82

NMR (DMSO-d$_6$) δ(ppm): 3.08(2H, m.), 3.25(2H, m), 3.31 (6H, s), 3.50(2H, m), 3.71(2H, t, J=5.2 Hz), 3.82–3.87)2H, m), 3.96–4.01(2H, m), 5.26(2H, s), 6.93 (1H, dd, J=1.2, 7.9 Hz), 7.36(1H, d, J=9.2 Hz), 7.75 (1H, d, J=7.9 Hz), 7.83(1H, t, J=8.1 Hz), 8.50(1H, d, J=9.2 Hz), 13.68(1H, s)

IR (KBr) cm$^{-1}$: 3400, 1657, 1625, 1595, 1575, 1513, 1468

EXAMPLE 43

2-(2-Aminoethyl)aminomethyl-5-bromo-7-methoxy-6H-pyrazolo-[4,5,1-d,e]acridin-6-one (Compound 43):

Compound 24 (1.00 g) and 2.2 ml of ethylenediamine were subjected to reaction in the same manner as in Example 40 to obtain 1.04 g (91.0%) of the hydrobromide of Compound 43.

NMR (DMSO-d$_6$) δ(ppm): 3.24–3.46(4H, m), 3.97(3H, s), 4.92(2H, s), 7.18(1H, dd, J=1.2, 8.3 Hz), 7.83(1H, dd, J=1.2, 8.0 Hz), 7.90(1H, t, J=8.3 Hz), 7.92(1H, d, J=8.3 Hz), 7.98(3H, brs), 8.35(1H, d, J=8.3 Hz), 9.55(1H, brs)

FAB-MS(m/z) 401$^+$+1); $C_{18}H_{17}BrN_4O_2=400$

EXAMPLE 44

2-(2-Aminoethyl)aminomethyl-5-bromo-7-hydroxy-6H-pyrazolo-[4,5,1-d,e]acridin-6-one (Compound 44):

Compound 43 (340 mg) was added to 4 ml of aqueous 48% hydrobromic acid solution and 6 ml of 25% hydrobromic acid/acetic acid solution, followed by stirring at 60° C. for one hour. After the reaction mixture was cooled, isopropanol was added thereto and the crystals precipitated were separated by filtration. To the crystals were added chloroform and diluted aqueous sodium carbonate solution for extraction, and the chloroform layer was concentrated and recrystallized from 4N HCl-ethanol to obtain 144 mg (48.2%) of the hydrochloride of Compound 44.

NMR (DMSO-d$_6$) δ(ppm): 3.29(2H, t, J=6.4 Hz), 3.47(2H, t, J=6.3 Hz), 4.88(2H, s), 6.95(1H, dd, J=0.9, 8.2 Hz), 7.66(1H, dd, J=0.9, 8.2 Hz), 7.86(1H, t, J=8.2 Hz), 7.98(1H, d, J=8.5 Hz), 8.43(3H, brs), 8.57 (1H, d, J=8.2 Hz), 10.20(1H, brs), 13.22(1H, s)

FAB-MS(m/z): 387(M$^+$+1); $C_{17}H_{15}BrN_4O_2=386$

EXAMPLE 45

2-(2-Aminoethyl)aminomethyl-5-[2-(2-hydroxyethylamino)ethyl]amino-7-methoxy-6H-pyrazolo[4,5,1-d,e]acridin-6-one (Compound 45):

Compound 43 (300 mg) and 3 ml of 2-(2-aminoethylamino)ethanol were subjected to reaction in the same manner as in Example 41 to obtain 142 mg (42.8%) of the hydrochloride of Compound 45.

NMR (DMSO-$d_6$) δ(ppm): 3.07(2H, m), 3.24–3.44(6H, m), 3.69(2H, t, J=5.1 Hz), 3.89–3.94(2H, m), 3.94(3H, s), 4.73(2H, s), 7.11(1H, dd, J=2.7, 6.8 Hz), 7.16 (1H, d, J=9.3 Hz), 7.80–7.88(2H, m), 8.34(1H, d, J=8.8 Hz), 9.87(1H, t, J=6.2 Hz)

FAB-MS(m/z) 425(M$^+$ + 1); $C_{22}H_{28}N_6O_3$ = 424

EXAMPLE 46

2-(2-Aminoethyl)aminomethyl-7-hydroxy-5-[2-(2-hydroxyethylamino)ethyl]amino-6H-pyrazolo[4,5,1-d,e]acridin-6-one (Compound 46):

Compound 45 (125 mg) was added to 12 ml of concentrated hydrochloric acid and subjected to reaction in the same manner as in Example 42 to obtain 112 mg (92.0%) of the hydrochloride of Compound 46.

NMR (DMSO-$d_6$) δ(ppm): 3.07(2H, m), 3.24–3.47(6H, m), 3.70(2H, t, J=5.0 Hz), 3.95–3.98(2H, m), 4.76(2H, s), 6.89(1H, dd, J=0.9, 8.2 Hz), 7.24(1H, d, J= 9.2 Hz), 7.67(1H, d, J=8.2 Hz), 7.81(1H, t, J=8.2 Hz), 8.47(1H, d, J=8.9 Hz), 9.27(1H, t, J=6.4 Hz), 13.71(1H, s)

EI-MS(m/z): 410(M$^+$); $C_{21}H_{26}N_6O_3$ = 410

EXAMPLE 47

5-[2-(2-Aminoethylamino)ethyl]amino-2-(2-aminoethyl)aminomethyl-7-methoxy-6H-pyrazolo[4,5,1-d,e]acridin-6-one (Compound 47):

Compound 43 (200 mg) and 2 ml of diethylenetriamine were subjected to reaction in the same manner as in Example 41 to obtain 130 mg (55.1%) of the hydrochloride of Compound 47.

NMR (DMSO-$d_6$) δ(ppm): 3.17–3.26(2H, m), 3.29–3.33(6H, m), 3.45(2H, t, J=6.4 Hz), 3.85–3.95(2H, m), 3.95 (3H, s), 4.74(2H, s), 7.13(1H, dd, J=2.3, 7.4 Hz), 7.20(1H, d, J=9.3 Hz), 7.82–7.91(2H, m), 8.31(1H, d, J=9.0 Hz), 8.36(4H, brs), 9.67(1H, brs), 9.87 (1H, t, J=6.2 Hz), 10.04(1H, brs)

EI-MS(m/z): 423(M$^{30}$); $C_{22}H_{29}N_7O_2$ = 423

EXAMPLE 48

5-[2-(2-Aminoethylamino)ethyl]amino-2-(2-aminoethyl)aminomethyl-7-hydroxy-6H-pyrazolo[4,5,1-d,e]acridin-6-one (Compound 48):

Compound 47 (110 mg) was added to 1.0 ml of aqueous 48% hydrobromic acid solution and 2 ml of 25% hydrobromic acid/acetic acid solution, followed by stirring at 100° C. for 3.5 hours. The reaction mixture was cooled and isopropanol was added thereto. The crystals precipitated were separated by filtration and then recrystallized from water-ethanol to obtain 81 mg (57.3%) of the hydrobromide of Compound 48.

NMR (DMSO-$d_6$) δ(ppm): 3.17–3.44(10H, m), 3.93–4.00(2H, m), 4.85(2H, s), 6.93(1H, d, J=8.2 Hz), 7.29(1H, d, J=9.5 Hz), 7.70(1H, d, J=8.2 Hz), 7.85(1H, t, J=8.2 Hz), 8.04(4H, brs), 8.43(1H, d, J=9.2 Hz), 9.02(1H, brs), 9.30(1H, t, J=5.4 Hz), 9.57(1H, brs), 13.72(1H, s)

FAB-MS(m/z): 410(M$^{30}$+ 1); $C_{21}H_{27}N_7O_2$ = 409

EXAMPLE 49

2-Bis(2-hydroxyethyl)aminomethyl-5-bromo-7-methoxy-6H-pyrazolo[4,5,1-d,e]acridin-6-one (Compound 49):

Compound 24 (200 mg) and 250 mg of diethanolamine were subjected to reaction in the same manner as in Example 40 to obtain 176 mg (83.2%) of Compound 49 as crystals.

NMR (DMSO-$d_6$) δ(ppm): 2.67(4H, t, J=5.9 Hz), 3.53(4H, q, J=5.9 Hz), 3.94(3H, s), 4.19(2H, s), 4.44(2H, t, J=4.9 Hz), 7.07(1H, dd, J=1.4, 8.0 Hz), 7.24(1H, d, J=8.1 Hz), 7.73(1H, dd, J=1.6, 8.2 Hz), 7.80(1H, t, J=8.2 Hz), 8.25(1H, d, J=8.2 Hz)

EI-MS(m/z): 445(M$^+$); $C_{20}H_{20}BrN_3O_4$ = 445

EXAMPLE 50

2-Bis(2-hydroxyethyl)aminomethyl-5-(2-dimethylaminoethyl)amino-7-methoxy-6H-pyrazolo[4,5,1-d,e]acridin-6-one (Compound 50):

Compound 49 (600 mg) and 10 ml of N,N-dimethylethylenediamine were stirred at 100° C. for one hour, and then the reaction mixture was concentrated to dryness. The residue was suspended in isopropyl alcohol and the suspension was filtered to obtain 543 mg (89.2%) of Compound 50 as crystals.

NMR (DMSO-$d_6$) δ(ppm): 2.33(6H, s), 2.50–2.52(6H, m), 3.51–3.55(6H, m), 3.93(3H, s), 4.08(2H, s), 6.86 (1H, d, J=9.0 Hz), 7.03(1H, dd, J=2.0, 7.3 Hz), 7.73–7.81(2H, m), 8.10(1H, d, J=8.8 Hz), 9.73(1H, t, J=5.1 Hz)

EI-MS(m/z): 453(M$^+$); $C_{24}H_{31}N_5O_4$ 32 453

EXAMPLE 51

2-Bis(2-hydroxyethyl)aminomethyl-5-(2-dimethylaminoethyl)amino-7-hydroxy-6H-pyrazolo[4,5,1-d,e]acridin-6-one (Compound 51):

Compound 50 (400 mg) was added to 30 ml of concentrated hydrochloric acid and subjected to reaction in the same manner as in Example 42 to obtain 420 mg (88.7%) of the hydrochloride of Compound 51.

NMR (DMSO-$d_6$) δ(ppm): 2.86(6H, s), 3.36–3.43(6H, m), 3.91(4H, t, J=4.9 Hz), 4.04(2H, q, J=6.4 Hz), 4.96 (2H, s), 6.90(1H, dd, J=0.9, 8.2 Hz), 7.27(1H, d, J=9.2 Hz), 7.67(1H, dd, J=0.9, 8.2 Hz), 7.81(1H, t, J=8.2 Hz), 8.42(1H, d, J=9.2 Hz), 9.25(1H, t, J=6.4 Hz), 13.66(1H, s)

EI-MS(m/z): 439(M$^+$); $C_{23}H_{29}N_5O_4$ = 439

EXAMPLE 52

5-(2-Aminoethyl)amino-2-bis(2-hydroxyethyl)aminomethyl-7-methoxy-6H-pyrazolo[4,5,1-d,e]acridin-6-one (Compound 52):

Compound 49 (400 mg) and 4 ml of ethylenediamine were subjected to reaction in the same manner as in Example 50 to obtain 325 mg (85.3%) of Compound 52 as crystals.

NMR (DMSO-$d_6$) δ(ppm): 2.65(4H, t, J=6.2 Hz), 2.87–2.91 (2H, m), 3.41–3.45(2H, m), 3.52(4H, t, J=6.2 Hz), 3.92(3H, s), 4.07(2H, s), 6.87(1H, d, J=9.0 Hz), 7.01(1H, dd, J=2.0, 7.3 Hz), 7.72–7.81(2H, m), 8.08(1H, d, J=8.8 Hz), 9.84(1H, t, J=4.5 Hz)

EI-MS(m/z): 425(M$^+$); $C_{22}H_{27}N_5O_4$ = 425

EXAMPLE 52

5-(2-Aminoethyl)amino-2-bis(2-hydroxyethyl)aminomethyl-7-hydroxy-6H-pyrazolo[4,5,1-d,e]acridin-6-one (Compound 53):

Compound 52 (300 mg) was added to 30 ml of concentrated hydrochloric acid and subjected to reaction in the same manner as in Example 42 to obtain 348 mg (93.4%) of the hydrochloride of Compound 53.

NMR (DMSO-d$_6$) δ(ppm): 3.09–3.12(2H, m), 3.43–3.44(4H, m), 3.89–3.92(6H, m), 4.96(2H, s), 6.90(1H, dd, J=0.9, 8.2 Hz), 7.25(1H, d, J=9.2 Hz), 7.68(1H, dd, J=0.9, 7.9 Hz), 7.81(1H, t, J=8.2 Hz), 8.40(1H, d, J=9.2 Hz), 9.28(1H, t, J=6.3 Hz), 13.70(1H, s)

EI-MS(m/z): 411(M$^+$); C$_{21}$H$_{25}$N$_5$O$_4$=411

EXAMPLE 54

2-Bis(2-chloroethyl)aminoethyl-5-(2-dimethylaminoethyl)amino-7-methoxy-6H-pyrazolo[4,5,1-d,e]acridin-6-one (Compound 54):

Compound 50 (50 mg) and 2 ml of thionyl chloride were subjected to reaction in the same manner as in Example 9 to obtain 52 mg (84.0%) of the hydrochloride of Compound 54.

NMR (DMSO-d$_6$) δ(ppm): 2.85(3H, s), 2.86(3H, s), 3.25 (4H, m), 3.38(2H, q, J=6.1 Hz), 3.46(2H, t, J=6.1 Hz), 3.95(3H, s), 4.20(4H, m), 4.48(2H, s), 7.07 (1H, d, J=5.1 Hz), 7.12(1H, d, J=8.8 Hz), 7.78–7.85 (2H, m), 8.23(1H, d, J=8.8 Hz), 9.82(1H, t, J=6.2 Hz)

FAB-MS(m/z): 490(M$^+$ +1); C$_{24}$H$_{29}$Cl$_2$N$_5$O$_2$=489

EXAMPLE 55

5-Bromo-2-bromomethyl-7-hydroxy-6H-pyrazolo[4,5,1-d,e]acridin-6-one (Compound 55):

Compound 24 (8.00 g) and 200 ml of 25% hydrobromic acid/acetic acid solution were subjected to reaction at 50° C. for 12 hours, followed by addition of 200 ml of water. The crystals precipitated were separated by filtration, washed with isopropyl alcohol and isopropyl ether, and then dried under reduced pressure to obtain 7.72 g (99.8%) of Compound 55 as crystals.

NMR (CDCl$_3$) δ(ppm): 4.90(2H, s), 6.90(1H, dd, J=1.5, 8.1 Hz), 7.59(1H, dd, J=1.2, 8.1 Hz), 7.67(1H, t, J=8.1 Hz), 7.78(1H, d, J=8.3 Hz), 8.03(1H, d, J=8.3 Hz), 13.20(1H, s)

EI-MS(m/z): 406(M$^+$); C$_{15}$H$_8$Br$_2$N$_2$O$_2$=406

EXAMPLE 56

7-Hydroxy- 5-(2-morpholinoethyl)amino-2-(2-morpholinoethyl)aminomethyl-6H-pyrazolo[4,5,1-d,e]acridin-6-one (Compound 56):

Compound 55 (150 mg) and 1 ml of N-(2-aminoethyl)morpholine were subjected to reaction at 65° C. for 40 minutes, and then the reaction mixture was concentrated to dryness. The resulting residue was recrystallized twice from concentrated hydrochloric acid-methanol-isopropanol to obtain 183 mg (80.8%) of the hydrochloride of Compound 56.

NMR (DMSO-d$_6$) δ(ppm): 3.20–3.73(14H, m), 3.80–4.10 (10H, m), 4.77(2H, s), 6.89(1H, dd, J=0.9, 8.2 Hz), 7.27(1H, d, J=9.5 Hz), 7.66(1H, dd, J=0.9, 8.2 Hz), 7.81(1H, t, J=8.2 Hz), 8.47(1H, d, J=9.2 Hz), 9.24 (1H, t, J=6.3 Hz), 10.18(1H, brs), 11.60(1H, brs), 13.67(1H, s)

EI-MS(m/z): 506(M$^+$); C$_{27}$H$_{34}$N$_6$O$_4$=506

EXAMPLE 57

5-Bromo-7-hydroxy-2-[2-(2-hydroxyethylthio)ethyl]aminomethyl-6H-pyrazolo[4,5,1-d,e]acridin-6-one (Compound 57):

Compound 55 (200 mg) was dissolved in 8 ml of chloroform, and 0.6 g of 2-(2-aminoethylthio)ethanol was added to the solution. The mixture was stirred at room temperature overnight. After washing with water, the reaction mixture was concentrated under reduced pressure. The resulting residue was subjected to silica gel column chromatography with chloroform-methanol (20:1) as the eluent to obtain 150 mg (68.3%) of Compound 57. The compound was converted into its hydrochloride by a conventional method using isopropanol solution containing hydrogen chloride.

NMR (DMSO-d$_6$) δ(ppm): 2.66(2H, t, J=6.5 Hz), 2.92(2H, t, J=7.6 Hz), 3.37(2H, t, J=7.6 Hz), 3.58(2H, t, J=6.5 Hz), 4.84(2H, s), 6.95(1H, dd, J=0.8, 8.2 Hz), 7.64(1H, d, J=7.3 Hz), 7.85(1H, t, J=8.2 Hz), 7.99 (1H, d, J=8.2 Hz), 8.51(1H, d, J=8.2 Hz), 9.74(2H, brs), 13.23(1H, s)

EI-MS(m/z): 447(M$^+$); C$_{19}$H$_{18}$BrN$_3$O$_3$S=447

EXAMPLE 58

7-Hydroxy-5-[2-(2-hydroxylthio)ethyl]amino-2-[2-(2-hydroxyethylthio)ethyl]aminomethyl-6H-pyrazolo[4,5,1-d,e]acridin-6-one (Compound 58):

Compound 55 (200 mg) and 0.6 g of 2-(2-aminoethylthio)ethanol were subjected to reaction in the same manner as in Example 57 to obtain 35 mg (14.6%) of Compound 58 as crystals.

NMR (DMSO-d$_6$) δ(ppm): 2.56(2H, t, J=6.9 Hz), 2.66(2H, t, J=6.4 Hz), 2.69(2H, t, J=6.6 Hz), 2.79(2H, t, J=6.4 Hz), 2.91(2H, t, J=6.7 Hz), 3.51(2H, t, J=6.9 Hz), 3.59(2H, t, J=6.5 Hz), 3.72(2H, q, J=6.5 Hz), 4.15(2H, s), 4.84(1H, t, J=5.5 Hz), 6.81(1H, d, J=7.9 Hz), 6.94(1H, d, J=9.2 Hz), 7.58(1H, d, J=8.2 Hz), 7.73(1H, t, J=8.2 Hz), 8.21(1H, d, J=8.9 Hz), 9.25(1H, t, J=6.0 Hz), 13.76(1H, s)

EI-MS(m/z): 488(M$^+$); C$_{23}$H$_{28}$N$_4$O$_4$S$_2$=488

EXAMPLE 59

5-(2-Aminoethyl)amino-7-hydroxy-2-[2-(2-hydroxyethylthio)ethyl]aminomethyl-6H-pyrazolo[4,5,1-d,e]acridin-6-one (Compound 59):

Compound 57 (150 mg) and 1 ml of ethylenediamine were subjected to reaction in the same manner as in Example 56 to obtain 131 mg (78.2%) of the hydrochloride of Compound 59.

NMR (DMSO-d$_6$) δ(ppm): 2.65(2H, t, J=6.6 Hz), 2.93(2H, t, J=6.7 Hz), 3.08–3.14(2H, m), 3.32–3.40(2H, m), 3.57(2H, t, J=6.6 Hz), 3.88(2H, q, J=6.3 Hz), 4.71 (2H, s), 6.89(1H, dd, J=0.9, 7.9 Hz), 7.23(1H, d, J=9.2 Hz), 7.66(1H, dd, J=0.9, 8.2 Hz), 7.81(1H, t, J=8.2 Hz), 8.22(3H, brs), 8.43(1H, d, J=8.9 Hz), 9.26(1H, t, J=6.3 Hz), 9.78(2H, brs), 13.73(1H, s) EI-MS(m/z): 427(M$^+$); C$_{21}$H$_{25}$N$_5$O$_3$S=427

EXAMPLE 60

5Bromo-7-hydroxy-2-[2-(2-hydroxyethyloxy)ethyl]aminomethyl-6H-pyrazolo[4,5,1-d,e]acridin-6-one (Compound 60):

Compound 55 (1.00 g) was dissolved in 200 ml of chloroform and 20 ml of dimethylformamide, and 5.2 g of 2-(2-aminoethoxy)ethanol was added to the solution, followed by stirring at room temperature for 3 hours. The reaction mixture was washed with water, and then the organic layer was concentrated under reduced pressure. The resulting residue was subjected to silica gel column chromatography with chloroform -methanol (20:1) as the eluent and then recrystallized from chloroform-isopropanol to obtain 814 mg (76.9%) of Compound 60.

NMR (CDCl$_3$) δ(ppm): 2.97(2H, t, J=5.0 Hz), 3.60–3.63 (2H, m), 3.69(2H, t, J=5.0 Hz), 3.74–3.77(2H, m), 4.35(2H, s), 6.88(1H, dd, J=2.1, 7.3 Hz), 7.61–7.70 (2H, m), 7.73(1H, d, J=8.2 Hz), 8.09(1H, d, J=8.2 Hz), 13.31(1H, brs)

FAB-MS(m/z); 432(M++1); $C_{19}H_{18}BrN_3O_4=431$

EXAMPLE 61

7-Hydroxy-5-[2-(2-hydroxyethyloxy)ethyl]amino-2-[2-(2-hydroxyethyloxy)ethyl]aminomethyl-6H-pyrazolo[4,5,1-d,e]acridin-6-one (Compound 61):

Compound 60 110 mg) and 1 ml of 2-(2-aminoethoxy)ethanol were subjected to reaction in the same manner as in Example 59 to obtain 121 mg (96.2%) of the hydrochloride of Compound 61.

NMR (DMSO-d$_6$) δ(ppm): 3.34(2H, t, J=5.0 Hz), 3.50–3.55 (8H, m), 3.72–3.79(6H, m), 4.65(2H, brs), 4.70(2H, s), 6.88(1H, dd, J=0.6, 8.2 Hz), 7.08(1H, d, J=8.2 Hz), 7.65(1H, d, J=8.2 Hz), 7.79(1H, t, J=8.2 Hz), 8.32(1H, d, J=8.9 Hz), 9.29–9.32(1H, m), 9.56(2H, brs), 13.66(1H, s)

EI-MS(m/z): 456(M+); $C_{23}H_{28}N_4O_6=456$

EXAMPLE 62

5-(2-Aminoethyl)amino-7-hydroxy-2-[2-(2-hydroxyethyloxy)ethyl]aminomethyl-6H-pyrazolo[4,5,1-d,e]acridin-6-one (Compound 62):

Compound 60 (135 mg) and 1 ml of ethylenediamine were subjected to reaction at 50° C. for one hour, followed by addition of 10 ml of isopropanol. The crystals precipitated were separated by filtration to obtain 120 mg (93.3%) of Compound 62. By recrystallization from concentrated hydrochloric acid-methanol-ethanol, the compound was converted into its hydrochloride.

NMR (DMSO-d$_6$) δ(ppm): 3.09–3.13(2H, m), 3.33(2H, t, J=5.2 Hz), 3 48–3.57(4H, m), 3.79(2H, t, J=5.2 Hz), 3.88(2H, q, J=6.3 Hz), 4.72(2H, s), 6.90(1H, dd, J=0.9, 8.2 Hz), 7.23(1H, d, J=9.2 Hz), 7.67(1H, dd, J=0.9, 8.2 Hz), 7.81(1H, t, J=8.2 Hz), 8.24(3H, brs), 8.42(1H, d, J=9.2 Hz), 9.27(1H, t, J=6.4 Hz), 9.68(2H, brs), 13.73(1H, s)

EI-MS(m/z): 411(M+); $C_{21}H_{25}N_5O_4=411$

EXAMPLE 63

5-(3-Aminopropyl)amino-7-hydroxy-2-[2-(2-hydroxyethyloxy)ethyl]aminomethyl-6H-pyrazolo[4,5,1-d,e]acridin-6-one (Compound 63):

Compound 60 (170 mg) and 1 ml of 1,3-diaminopropane were subjected to reaction in the same manner as in Example 62 to obtain 140 mg (74.0%) of the hydrochloride of Compound 63.

NMR (DMSO-d$_6$) δ(ppm): 2.00(2H, quint, J=7.0 Hz), 2.89–2.97(2H, m), 3.33(2H, t, J=5.0 Hz), 3.48–3.56(4H, m), 3.69(2H, q, J=6.6 Hz), 3.78(2H, t, J=5.2 Hz), 4.71(2H, s), 6.89(1H, dd, J=0.9, 8.2 Hz), 7.13(1H, d, J=9.2 Hz), 7.66(1H, dd, J=0.9, 8.2 Hz), 7.81(1H, t, J=8.2 Hz), 8.09(3H, brs), 8.38(1H, d, J=9.2 Hz), 9.27(1H, t, J=6.0 Hz), 9.65(2H, brs), 13.71(1H, s)

EI-MS(m/z): 425(M+); $C_{22}H_{27}N_5O_4=425$

EXAMPLE 64

5-(2-Dimethylaminoethyl)amino-7-hydroxy-2-[2-(2-hydroxyethyloxy)ethyl]aminomethyl-6H-pyrazolo[4,5,1-d,e]acridin-one (Compound 64):

Compound 60 (170 mg) and 1 ml of N,N-dimethylethylenediamine were subjected to reaction in the same manner as in Example 62 to obtain 116 mg (57.5%) of the hydrochloride of Compound 64.

NMR (DMSO-d$_6$) δ(ppm): 2.86(6H, s), 3.33(2H, t, J=4.9 Hz), 3.40(2H, t, J=6.6 Hz), 3.49–3.57(4H, m), 3.78 (2H, t, J=5.0 Hz), 4.03(2H, q, J=6.7 Hz), 4.73(2H, s), 6.91(1H, dd, J=0.9, 8.2 Hz), 7.26(1H, d, J=9.2 Hz), 7.68(1H, dd, J=0.9, 8.2 Hz), 7.82(1H, t, J=8.2 Hz), 8.43(1H, d, J=8.9 Hz), 9.26(1H, t, J=6.7 Hz), 9.63(2H, brs), 10.68(1H, brs), 13.71(1H, s)

EI-MS(m/z): 439(M+); $C_{29}H_{29}N_5O_4=439$

EXAMPLE 65

7-Hydroxy-2-[2-(2-hydroxyethyloxy)ethyl]aminomethyl-5-(2-methylaminoethyl)amino-6H-pyrazolo[4,5,1-d,e]acridin-6-one (Compound 65):

Compound 60 (170 mg) was dissolved in 1.7 ml of dimethylformamide, and 410 mg of N-benzyloxycarbonyl-N-methylethylenediamine was added to the solution, followed by stirring at 80° C. for 4 hours. Water and chloroform were added to the reaction mixture for extraction, and the chloroform layer was concentrated under reduced pressure. The residue was subjected to silica gel column chromatography with chloroform-methanol (9:1) as the eluent and then crystallized from chloroform-isopropanol-diisopropyl ether to obtain 156 mg (70.8%) of 5-[2-(N-benzyloxycarbonyl-N-methyl)aminoethyl]amino-7-hydroxy-2-[2-(2-hydroxyethyloxy)ethyl]aminomethyl-6H-pyrazolo[4,5,1-d,e]acridin-6-one. To 145 mg of the obtained compound were added 2 ml of methanol and 6 ml of concentrated hydrochloric acid, and the mixture was stirred at 90° C. for 3 hours. The reaction mixture was then concentrated under reduced pressure, and the residue was recrystallized from methanol-isopropanol to obtain 96 mg (74.1%) of the hydrochloride of Compound 65.

NMR (DMSO-d$_6$) δ(ppm): 2.61(3H, s), 3.23(2H, t, J=6.4 Hz), 3.30(2H, t, J=5.2 Hz), 3.46–3.57(4H, m), 3.77 (2H, t, J=5.3 Hz), 3.95(2H, q, J=6.2 Hz), 4.67(2H, s), 6.89(1H, dd, J=0.9, 8.2 Hz), 7.24(1H, d, J=9.2 Hz), 7.66(1H, dd, J=0.9, 8.2 Hz), 7.81(1H, t, J=8.2 Hz), 8.41(1H, d, J=9.2 Hz), 9.25(1H, t, J=6.3 Hz), 13.70(1H, s)

FAB-MS(m/z): 426(M+30 1); $C_{22}H_{27}N_5O_4=425$

EXAMPLE 66

7-Hydroxy-5-[2-(2-hydroxyethylamino)ethyl]amino-2-[2-(2-hydroxyethyloxy)ethyl]aminomethyl-6H-pyrazolo[4,5,1-d,e]acridin-6-one (Compound 66):

Compound 60 (145 mg) and 1 ml of 2-(2-aminoethylamino)ethanol were subjected to reaction in the same manner as in Example 62 to obtain 155 mg (87.4%) of the hydrochloride of Compound 66.

NMR (DMSO-d$_6$) δ(ppm): 3.09(2H, t, J=5.2 Hz), 3.26(2H, t, J=6.1 Hz), 3.33(2H, t, J=5.2 Hz), 3.49–3.55(4H, m), 3.70(2H, t, J=4.9 Hz), 3.78(2H, t, J=5.0 Hz), 3.93–4.01(2H, m), 4.72(2H, s), 5.33(1H, brs), 6.90(1H, dd, J=0.9, 8.2 Hz), 7.25(1H, d, J=9.5 Hz), 7.67(1H, dd, J=0.9, 8.2 Hz), 7.81(1H, t, J=8.2 Hz), 8.43(1H, d, J=8.9 Hz), 9.11(2H, brs), 9.28(1H, t, J=6.1 Hz), 9.69(2H, brs), 13.72(1H, s)

EI-MS(m/z): 407(M+); $C_{23}H_{29}N_5O_2=407$

EXAMPLE 67

5-Bromo-7-hydroxy-2-(2-hydroxyethyl)aminomethyl-6H-pyrazolo[4,5,1-d,e]acridin-6-one (Compound 67):

Compound 55 (500 mg) and 1.5 g of ethanolamine were subjected to reaction in the same manner as in Example to obtain 345 mg (73.0%) of Compound 67 as crystals.

NMR (DMSO-d$_6$) δ(ppm): 2.69(2H, t, J=5.6 Hz), 3.51(2H, q, J=5.3 Hz), 4.28(2H, s), 4.55(1H, t, J=5.3 Hz), 6.87(1H, dd, J=0.7, 8.2 Hz), 7.59(1H, dd, J=0.7, 8.2 Hz), 7.80(1H, t, J=8.2 Hz), 7.87(1H, d, J=8.1 Hz), 8.40(1H, d, J=8.2 Hz)

EI-MS(m/z): 387(M+); $C_{17}H_{14}BrN_3O_3=387$

EXAMPLE 68

5-(2-Aminoethyl)amino-7-hydroxy-2-(2-hydroxyethyl)aminomethyl-6H-pyrazolo[4,5,1-d,e]acridin-6-one (Compound 68):

Compound 67 (150 mg) and 1 ml of ethylenediamine were subjected to reaction in the same manner as in Example 62 to obtain 144 mg (84.8%) of the hydrochloride of Compound 68.

NMR (DMSO-$d_6$) δ(ppm): 3.07-3.13(2H,.m), 3.19(2H, t, J=5.2 Hz), 3.76(2H, t, J=5.0 Hz), 3.88(2H, q, J=6.1 Hz), 4.70(2H, s), 5.31(1H, brs), 6.89(1H, dd, J=0.9, 8.2 Hz), 7.23(1H, d, J=9.2 Hz), 7.66(1H, dd, J=0.9, 8.2 Hz), 7.81(1H, t, J=8.2 Hz), 8.26(3H, brs), 8.41(1H, d, J=8.9 Hz), 9.26(1H, t, J=6.4 Hz), 9.63(2H, brs), 13.73(1H, s)

EI-MS(m/z): 367(M+); $C_{19}H_{21}N_5O_3=367$

EXAMPLE 69

7-Hydroxy-5-[2-(2-hydroxyethylamino)ethyl]amino-2-(2-hydroxyethyl)aminomethyl-6H-pyrazolo[4,5,1-d,e]acridin-6-one (Compound 69):

Compound 67 (150 mg) and 1 ml of 2-(2-aminoethylamino)ethanol were subjected to reaction in the same manner as in Example 62 to obtain 168 mg (89.9%) of the hydrochloride of Compound 69.

NMR (DMSO-$d_6$) δ(ppm): 3.07-3.14(2H, m), 3.19-3.26(4H, m), 3.70(2H, t, J=5.2 Hz), 3.76(2H, t, J=5.3 Hz), 3.97(2H, q, J=6.4 Hz), 4.70(2H, s), 5.33(1H, brs), 6.89(1H, dd, J=0.9, 8.2 Hz), 7.25(1H, d, J=9.2 Hz), 7.66(1H, dd, J=0.9, 8.2 Hz), 7.81(1H, t, J=8.2 Hz), 8.42(1H, d, J=9.2 Hz), 9.12(2H, brs), 9.28(1H, t, J=6.4 Hz), 9.62(2H, brs), 13.73(1H, s)

FAB-MS(m/z): 412(M++1); $C_{21}H_{25}N_5O_4=411$

EXAMPLE 70

5-(3-Dimethylaminopropyl)amino-2-(3-dimethylaminopropyl)aminomethyl-7-hydroxy-6H-pyrazolo[4,5,1-d,e]acridin-6-one (Compound 70):

Compound 55 (150 mg) and 1 ml of N,N-dimethyl-1,3-propanediamine were subjected to reaction at 65° C. for 40 minutes, and the reaction mixture was concentrated to dryness. The resulting residue was extracted with water and chloroform, and the chloroform layer was concentrated and recrystallized from concentrated hydrochloric acid-methanol-isopropanol to obtain 102 mg (49.5%) of the hydrochloride of Compound 70.

NMR (DMSO-$d_6$) δ(ppm): 2.06-2.26(4H, m), 2.75(6H, s), 2.76(6H, s), 3.15-3.24(6H, m), 3.65-3.72(2H, m), 4.67(2H, s), 6.89(1H, dd, J=3.1, 8.2 Hz), 7.13(1H, dd, J=5.6, 8.7 Hz), 7.66(1H, dd, J=4.7, 8.2 Hz), 7.81(1H, dt, J=2.8, 8.0 Hz), 8.45(1H, d, J=9.2 Hz), 9.22-9 29(1H, m), 9.97(1H, brs), 10.80(1H, brs), 13.71(1H, d, J=5.1 Hz)

EI-MS(m/z): 450(M+); $C_{25}H_{34}N_6O_2=450$

EXAMPLE 71

2-Diethylaminomethyl-5-(2-dimethylaminoethyl)amino-7-hydroxy-6H-pyrazolo[4,5,1-d,e]acridin-6-one (Compound 71):

Compound 55 (200 mg) was dissolved in 20 ml of chloroform, and 1 ml of diethylamine was added to the solution. The mixture was subjected to reaction at room temperature for 3 hours. The reaction mixture was then concentrated and recrystallized from chloroform-ethanol to obtain 158 mg (80.8%) of 5-bromo-2-diethylaminomethyl-7-hydroxy-6H-pyrazolo[4,5,1-d,e]acridin-6-one.

The obtained compound (145 mg) and 1.5 ml of N,N-dimethylethylenediamine were subjected to reaction in the same manner as in Example 62 to obtain 154 mg (88.4%) of the hydrochloride of Compound 71.

NMR (DMSO-$d_6$) δ(ppm): 1.37(6H, t, J=7.2 Hz), 2.86(6H, s), 3.27(4H, q, J=7.0 Hz), 3.40(2H, t, J=6.9 Hz), 4.04(2H, q, J=6.6 Hz), 4.82(2H, s), 6.91(1H, dd, J=1.1, 8.2 Hz), 7.27(1H, d, J=9.2 Hz), 7.67(1H, dd, J=0.9, 8.2 Hz), 7.81(1H, t, J=8.2 Hz), 8.42(1H, d, J=8.9 Hz), 9.26(1H, t, J=6.4 Hz), 10.87(1H, brs), 11.08(1H, brs), 13.66(1H, s)

EI-MS(m/z): 407(M+); $C_{23}H_{29}N_5O_2=407$

EXAMPLE 72

5-Methoxy-2-methyl-6H-pyrazolo[4,5,1-d,e]acridin-6-one (Compound 72):

5-Bromo-2-methyl-6H-pyrazolo[4,5,1-d,e]acridin-6-one (8.52 g) obtained in Example 20 was dissolved in 800 ml of absolute methanol and 550 ml of absolute dioxane. To the solution was added 4.41 g of sodium methoxide, and the mixture was heated under reflux with stirring for 1.5 hours. The reaction mixture was concentrated under reduced pressure, and the residue was dissolved in chloroform. The solution was washed with 10% citric acid, saturated aqueous sodium bicarbonate solution and saturated aqueous sodium chloride solution, and thereafter dried over anhydrous sodium sulfate. The chloroform layer was concentrated under reduced pressure, and the residue was subjected to silica gel column chromatography with chloroform-acetone (20:1) as the eluent and then crystallized from chloroform-n-hexane to obtain 6.00 g (83.5%) of Compound 72.

NMR (DMSO-$d_6$) δ(ppm): 2.69(3H, s), 4.08(3H, s), 7.29 (1H, d, J=7.8 Hz), 7.49(1H, ddd, J=1.1, 7.6, 7.6 Hz), 7.88(1H, ddd, J=1.4, 7.1, 8.3 Hz), 8.14(1H, dd, J=0.7, 8.2 Hz), 3.23(1H, d, J=8.1 Hz), 8.29(1H, dd, J=1.1, 8.1 Hz)

EI-MS(m/z): 264(M+); $C_{16}H_{12}N_2O_2=264$

EXAMPLE 73

2-Bromomethyl-5-methoxy-6H-pyrazolo[4,5,1-d,e]acridin-6-one (Compound 73):

Compound 72 (0.39 g) was dissolved in 335 ml of carbon tetrachloride, and 318 mg of N-bromosuccinimide and mg of benzoyl peroxide were added to the solution. The mixture was heated under reflux with stirring for 18 hours. The reaction mixture was concentrated and then purified by silica gel column chromatography with chloroform-methanol (100:1) as the eluent to obtain 0.24 g (47.0%) of Compound 73.

NMR (DMSO-$d_6$) δ(ppm): 4.20(3H, s), 4.98(2H, s), 7.27 (1H, d, J=8.8 Hz), 7.67(1H, dd, J=7.3, 8.1 Hz), 7.82(1H, t, J=7.3 Hz), 8.22(1H, d, J=8.2 Hz), 8.27 (1H, d, J=8.8 Hz), 8.44(1H, dd, J=0.9, 8.1 Hz), EI-MS(m/z): 342(M+); $C_{16}H_{11}BrN_2O_2=343$

EXAMPLE 74

2-Bromomethyl-5-hydroxy-6H-pyrazolo[4,5,1-d,e]acridin-6-one (Compound 74):

To 417 mg of Compound 73 was added 10 ml of 25% hydrobromic acid/acetic acid solution, and the mixture was heated under reflux with stirring for 20 minutes. The reaction mixture was concentrated under reduced pressure, and the residue was dissolved in chloroform. The resulting solution was washed with saturated aqueous sodium bicarbonate solution and saturated aqueous sodium chloride solution, and then dried over anhydrous sodium sulfate. The chloroform layer was concentrated under reduced pressure, and the residue was crystallized from methanol-dichloromethane to obtain 274 mg (68.5%) of Compound 74.

NMR (CDCl$_3$; 90 Mz) δ(ppm): 4.89(2H, s), 7.07(1H, d, J=8.80 Hz), 7.48(1H, ddd, J=1.5, 5.5, 8.2 Hz.), 7.86 (1H, ddd, J=1.5, 6.9, 7.3 Hz), 8.13(1H, d, J=8.6 Hz), 8.28(1H, dd, J=0.8, 8.2 Hz), 8.47(1H, ddd, J=1.5, 7.9 Hz), 11.62(1H, brs)

EXAMPLE 75

2-(2-Aminoethyl)aminomethyl-5-methoxy-6H-pyrazolo[4,5,1-d,e]acridin-6-one (Compound 75):

Compound 73.(300 mg) was dissolved in 70 ml of absolute chloroform, and 1.70 g of N-benzyloxycarbonylethylenediamine was added to the solution. The mixture was stirred at room temperature for 18 hours and then heated under reflux with stirring for 11 hours. The reaction mixture was washed with water and saturated aqueous sodium chloride solution, and then dried over anhydrous sodium sulfate, followed by concentration under reduced pressure. The resulting residue was purified by silica gel column chromatography with chloroform -methanol (30:1) as the eluent to obtain 317 mg (79.4%) of 2-(2-benzyloxycarbonylaminoethyl)aminomethyl-5-methoxy-6H-pyrazolo[4,5,1-d,e]acridin-6-one.

To 316 mg of the obtained compound was added 10 ml of 25% hydrobromic arid/acetic acid solution, followed by stirring at room temperature for 25 minutes. The precipitate formed was separated by filtration and recrystallized from water-methanol-ethanol to obtain 248 mg (73.8%) of the hydrobromide of Compound 75.

NMR (D$_2$O) δ(ppm): 3.56(2H, t, J=6.6 Hz), 3.70(2H, t, J=6 9 Hz), 3.98(2H, s), 4.68(3H, s), 6.89(1H, d, J=9.0 Hz), 7.30(1H, brs), 7.66(2H, brs), 7.75(1H, dd, J=2.4, 6.1 Hz), 7.89(1H, dd, J=3.5, 7.2 Hz)

EI-MS(m/z): 322(M+); C$_{18}$H$_{18}$N$_4$O$_2$=322

EXAMPLE 76

2-(2-Aminoethyl)aminomethyl-5-hydroxy-6H-pyrazolo[4,5,1-d,e]acridin-6-one (Compound 76):

To 120 mg of Compound 75 was added 5 ml of 25% hydrobromic acid/acetic acid solution, and the mixture was heated under reflux with stirring for 2 hours. The reaction mixture was concentrated under reduced pressure, and the resulting residue was recrystallized from water-methanol-ethanol to obtain 86.8 mg (75.6%) of the hydrobromide of Compound 76.

NMR (DMSO-d$_6$) δ(ppm): 3.25(2H, t, J=6.3 Hz), 3.45(2H, t, J=6.9 Hz), 4.91(2H, s), 7.25(1H, d, J=8.6 Hz), 7.64(1H, ddd, J=1.4, 7.5, 8.4 Hz), 8.06(1H, ddd, J=1.3, 7.2, 8.4 Hz), 8.31(1H, d, J=8.1 Hz), 8.41(1H, dd, J=1.1, 7.9 Hz), 8.47(1H, d, J=8.6 Hz)

EI-MS(m/z): 308(M+); C$_{17}$H$_{16}$N$_4$O$_2$32 308

EXAMPLE 77

2-Bis-(2-hydroxyethyl)aminomethyl-5-methoxy-6H-pyrazolo[4,5,1-d,e]acridin-6-one (Compound 77):

Compound 73 (0.60 g) was dissolved in 35 ml of chloroform, and 2.8 ml of bis(ethanol)amine was added to the solution. The mixture was heated under reflux with stirring for 40 minutes. The reaction mixture was washed with water and saturated aqueous sodium chloride solution and then dried over anhydrous sodium sulfate, followed by concentration under reduced pressure. The resulting residue was purified by silica gel column chromatography with chloroform-methanol (200:1) as the eluent to obtain 0.28 g (58.1%) of Compound 77. The compound thus obtained (0.14 g) was dissolved in chloroform and several drops of 5N hydrochloric acid/isopropanol was added to the solution. The precipitate formed was separated by filtration to obtain 112 mg (36.5%) of the hydrochloride of Compound 77.

NMR (DMSO-d$_6$) δ(ppm): 3.13(4H, brs), 3.48(4H, brs), 4.12 (2H, s), 4.60(3H, s), 7.37(1H, d, J=9.0 Hz), 7.55 (1H, t, J=7.6 Hz), 7.94(1H, t, J=7.7 Hz), 8.22(1H, d, J=8.3 Hz), 8.32(1H, dd, J=1.3, 7.2 Hz), 8.42(1H, d, J=8.8 Hz)

EI-MS(m/z): 367(M+); C$_{20}$H$_{21}$N$_3$O$_4$=367

EXAMPLE 78

2-Bis(2-chloroethyl)aminomethyl-5-methoxy-6H-pyrazolo[4,5,1-d,e]acridin-6-one (Compound 78):

Compound 77 in the free form (0.15 g) was dissolved in 41 ml of chloroform, and 5.5 ml of thionyl chloride was added to the solution. The mixture was stirred with ice-cooling for 10 minutes and then at room temperature for 1.5 hours. The reaction mixture was concentrated under reduced pressure, and the residue was dissolved in chloroform. The resulting solution was washed with saturated aqueous sodium bicarbonate solution and saturated aqueous sodium chloride solution and then dried over anhydrous sodium sulfate, followed by concentration under reduced pressure. The resulting residue was subjected to silica gel column chromatography with chloroform-methanol (200:1) as the eluent and crystallized from chloroform-n-hexane to obtain 111 mg (72.2%) of Compound 78.

NMR (DMSO-d$_6$) δ(ppm): 3.09(2H, t, J=6.6 Hz), 3.65(2H, t, J=6.6 Hz), 4.19(3H, s), 4.28(2H, s), 7.12(1H, d, J=8.8 Hz), 7.44(1H, ddd, J=1.1, 7.2, 8.1 Hz), 7.79 (1H, ddd, J=1.4, 7.7, 8.1 Hz), 8.22(1H, dd, J=0.6, 8.3 Hz), 8.35(1H, d, J=8.8 Hz), 8.53(1H, dd, J=1.5, 7.9 Hz)

EI-MS(m/z) 403(M+); C$_{20}$H$_{19}$Cl$_2$N$_3$O$_2$=403

EXAMPLE 79

5-(2-Aminoethyl)amino-2-(2-aminoethyl)thiomethyl-6H-pyrazolo[4,5,1-d,e]acridin-6-one (Compound 79):

Compound 20 (322 mg) was dissolved in 26 ml of absolute tetrahydrofuran, and 276 mg of N-triphenylmethylaminoethanethiol and 36.2 mg of 60% sodium hydride were added to the solution. The mixture was stirred with ice-cooling for 40 minutes and then at room temperature for 7.5 hours. After addition of 50 ml of dichloromethane, the reaction mixture was washed with 10% citric acid and saturated aqueous sodium chloride solution. The organic layer was dried over anhydrous magnesium sulfate and concentrated under reduced pressure. The resulting residue was purified by silica gel column chromatography with hexane-ethyl acetate (7:1) as the eluent to obtain 277 mg (53.4%) of 5-bromo-2-(2-triphenylmethylaminoethyl)aminomethyl-6H-pyrazolo[4,5,1-d,e]acridin-6-one.

The obtained compound (123 mg) was dissolved in 2.5 ml of absolute chloroform, and 0.5 ml of ethylenediamine was added to the solution. The mixture was heated under reflux with stirring for 3.5 hours. The reaction mixture was washed with water and saturated aqueous sodium chloride solution and dried over anhydrous sodium sulfate, followed by concentration under reduced pressure. The residue was purified by silica gel column chromatography with chloroform-methanol (9:1) as the eluent to obtain 109 mg (91.8%) of 5-(2- aminoethyl)amino-2-(2-triphenylmethylaminoethyl)thiomethyl-6H-pyrazolo[4,5,1-d,e]acridin-6-one.

To 90 mg of the obtained compound was added 1 ml of 99% formic acid, followed by stirring at room temperature for 40 minutes. The reaction mixture was concentrated under reduced pressure, and water was added to the residue. After the insoluble substance was removed, the water layer was concentrated under reduced pressure, and the residue was crystallized from water-ethanol to obtain 52.2 mg (72.5%) of the diformate of Compound 79.

NMR (DMSO-d$_6$) δ(ppm): 2.72(2H, t, J=6.8 Hz), 2.95(4H, m), 3.65(2H, m), 4.24(2H, s), 7.03(1H, d, J=8.8 Hz), 7.53(1H, t, J=7.6 Hz), 7.91(1H, t, J=7.7 Hz), 8.16 (1H, d, J=9.0 Hz), 8.22(1H, d, J=8.1 Hz), 8.35(2H, s), 8.37(1H, d, J=7.1 Hz), 9.64(1H, brs)

EI-MS(m/z): 367(M+); C$_{19}$H$_{21}$N$_5$OS=367

EXAMPLE 80

2-(2-Aminoethyl)thiomethyl-5-(2-dimethylaminoethyl)amino-6H-pyrazolo[4,5,1-d,e]acridin-6-one (Compound 80):

5-Bromo-2-(2-triphenylmethylaminoethyl)aminomethyl-6H-pyrazolo[4,5,1-d,e]acridin-6-one (142 mg) obtained in Example 79 was dissolved in 2 ml of absolute chloroform, and 0.75 ml of N,N-dimethylethylenediamine was added to the solution. The mixture was treated in the same manner as in Example 79 to obtain 143 mg (97.7%) of 5-(2-dimethylaminoethyl)amino-2-(2-triphenylmethylaminoethyl)aminomethyl-6H-pyrazolo[4,5,1-d,e]acridin-6-one.

The obtained compound (140 mg) and 1.5 ml of 99% formic acid were subjected to the same treatments as in Example 79 to obtain 35 mg (32.7%) of the diformate of Compound 80.

NMR (DMSO-d$_6$) δ(ppm): 2.27(6H, s), 2.62(2H, t, J=6.0 Hz), 2.75(2H, t, J=7.1 Hz), 3.00(1H, t, J=6.6 Hz), 3.55(2H, q, J=5.6 Hz), 4.25(2H, s), 6.94(1H, d, J=9.0 Hz), 7.52(1H, t, J=7.6 Hz), 7.90(1H, t, J=7.7 Hz), 8.15(1H, d, J=8.8 Hz), 8.22(1H, d, J=8.3 Hz), 8.39 (1H, d, J=8.1 Hz), 9.62(1H, t, J=4.9 Hz)

EI-MS(m/z): 395(M+); C$_{21}$H$_{25}$N$_5$OS=395

EXAMPLE 81

2-(2-Aminoethyl)aminomethyl-5,7-dimethoxy-6H-pyrazolo[4,5,1-d,e]acridin-6-one (Compound 81):

5-Bromo-7-methoxy-2-methyl-6H-pyrazolo[4,5,1-d,e]acridin-6-one (50 mg) obtained in Example 24 was dissolved in 1 ml of absolute methanol and 2 ml of absolute dioxane, and 30 mg of 28% sodium methoxide/methanol solution was added to the solution. The mixture was heated under reflux with stirring for 2 hours, followed by addition of chloroform. The reaction mixture was washed with 10% citric acid and saturated aqueous sodium chloride solution, dried over anhydrous sodium sulfate, and then concentrated under reduced pressure. The crystals precipitated were separated by filtration to obtain 31.8 mg (77.7%) of 5,7-dimethoxy-2-methyl-6H-pyrazolo[4,5,1-d,e]acridin-6-one.

The obtained compound (1.01 g), 0.67 g of N-bromosuccinimide and 0.10 g of benzoyl peroxide were dissolved in 600 ml of carbon tetrachloride. The solution was treated in the same manner as in Example 73 to obtain 0.61 g (47.7%) of 2-bromomethyl-5,7-dimethoxy-6H-pyrazolo[4,5,1-d,e]acridin-6-one.

The obtained compound (104 mg) was dissolved in 5 ml of absolute dimethylformamide, and 177 mg of ethylenediamine was added to the solution, followed by stirring at room temperature for 20 minutes. The reaction mixture was concentrated under reduced pressure, and the resulting residue was washed with isopropanol and then dissolved in methanol. To the solution was added several drops of 5N hydrochloric acid/isopropanol solution. The crystals precipitated were separated by filtration and recrystallized from water-methanol-ethanol to obtain 100.0 mg (84.3%) of the dihydrochloride of Compound 81.

NMR (DMSO-d$_6$) δ(ppm): 3.29(2H, t, J=5.1 Hz), 3.45(2H, t, J=5.9 Hz), 3.92(3H, s), 4.07(3H, s), 4.81(2H, s), 7.10(1H, dd, J=3.9, 9.5 Hz), 7.40(1H, d, J=9.0 Hz), 7.81(2H, d, J=4.5 Hz), 8.39(1H, brs), 8.52(1H, d, J=8.8 Hz)

EI-MS(m/z): 352(M+); C$_{19}$H$_{20}$N$_4$O$_3$=352

EXAMPLE 82

2-Bis-(2-hydroxyethyl)aminomethyl-5,7-dimethoxy-6H-pyrazolo[4,5,1-d,e]acridin-6-one (Compound 82):

2-Bromomethyl-5,7-dimethoxy-6H-pyrazolo[4,5,1-d,e]acridin-6-one (200 mg) obtained in Example 81 was dissolved in 5 ml of absolute N,N-dimethylformamide, and 563 mg of bis(ethanol)amine was added to the solution. The reaction mixture was treated in the same manner as in Example 81 to obtain 96.5 mg (38.3%) of the dihydrochloride of Compound 82.

NMR (DMSO-d$_6$) δ(ppm): 2.94(4H, t, J=5.1 Hz), 3.74(4H, t, J=5.1 Hz), 4.02(3H, s), 4.12(3H, s), 4.28(2H, s), 6.88(1H, d, J=8.1 Hz), 7.06(1H, d, J=8.8 Hz), 7.65(1H, t, J=8.3 Hz), 7.80(1H, d, J=8.1 Hz), 8.05 (1H, d, J=8.8 Hz)

EI-MS(m/z): 397(M+); C$_{21}$H$_{23}$N$_3$O$_5$=397

EXAMPLE 83

2-(2-Aminoethyl)amino-5,7-dihydroxy-6H-pyrazolo[4,5,1-d,e]acridin-6-one (Compound 83):

2-Bromomethyl-5,7-dimethoxy-6H-pyrazolo[4,5,1-d,e]acridin-6-one (300 mg) obtained in Example 81 was dissolved in 20 ml of absolute dichloroethane, and 2.4 ml of 1M boron tribromide/diethyl ether solution was added to the solution under cooling at −78° C. The reaction mixture was stirred at 80° C. for 2 hours and then poured into ice-water, followed by addition of chloroform for extraction. The chloroform layer was washed with water, dried over anhydrous sodium sulfate and then concentrated under reduced pressure. The residue was purified by silica gel column chromatography with chloroform as the eluent to obtain 224 mg (81.2%) of 2-bromomethyl-5,7-dihydroxy-6H-pyrazolo[4,5,1-d,e]acridin-6-one.

To 100 mg of the obtained compound was added 180 mg of ethylenediamine, and the mixture was treated in the same manner as in Example 81 to obtain 108 mg (92.0%) of the dihydrochloride of Compound 83.

NMR (DMSO-d$_6$) δ(ppm): 3.28(2H, t, J=6.4 Hz), 3.46(2H, t, J=6.6 Hz), 4.83(2H, s), 6.93(1H, dd, J=0.9, 8.2 Hz), 7.23(1H, d, J=8.9 Hz), 7.68(1H, dd, J=0.9, 8.2 Hz), 7.85(1H, t, J=8.2 Hz), 8.49(1H, dd, J=0.9, 8.7 Hz)

EI-MS(m/z): 324(M+); C$_{17}$H$_{16}$N$_4$O$_3$=324

EXAMPLE 84

2-Bis-(2-hydroxyethyl)amino-5-hydroxy-6H-pyrazolo[4,5,1-d,e]acridin-6-one (Compound 84):

Compound 74 (190 mg) was dissolved in 6 ml of absoluble chloroform, and 1 ml of bis(ethanol)amine was added to the solution. The mixture was treated in the same manner as in Example 77 to obtain 49 mg (21.6%) of the monohydrochloride of Compound 84.

NMR (DMSO-d$_6$) δ(ppm): 3.48(4H, t, J=5.1 Hz), 3.92(4H, t, J=5.1 Hz), 5.01(2H, s), 7.23(1H, d, J=8.8 Hz), 7.62(1H, t, J=7.6 Hz), 8.02(1H, t, J=8.3 Hz), 8.34 (1H, d, J=7.8 Hz), 8.39(1H, dd, J=1.2, 8.1 Hz), 8.48(1H, d, J=8.8 Hz), 10.42(1H, brs)

EI-MS(m/z): 354(M$^+$ +1); C$_{19}$H$_{19}$N$_3$O$_4$=353

REFERENCE EXAMPLE 1

Preparation of injection:

Compound 28 (5 mg) is put in a sterilized 10-ml brown vial to prepare a sterilized powder preparation. Before use, 5 ml of sterilized physiological saline solution is added thereto and the mixture is well shaken and stirred to dissolve the compound. An injection is thus prepared.

REFERENCE EXAMPLE 2

Preparation of tablets:

Compound 29 (10 mg), 170 mg of lactose, 20 mg of potato starch, 4 mg of hydroxypropyl cellulose and 1 mg of magnesium stearate are blended and formed into a tablet by a conventional method.

REFERENCE EXAMPLE 3

Preparation of suppositories:

Compound 22 (20 mg), 750 mg of Witepsol H-15 (Dynamit Nobel) and 320 mg of Witepsol E-75 (Dynamit Nobel) are blended and formed into a suppository by a conventional method.

What is claimed is:

1. Compounds of the formula:

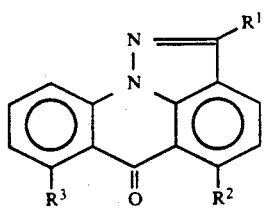

wherein

R$^1$ represents —CH$_2$X in which X represents halogen, —NR$^{4a}$R$^{4b}$ (wherein R$^{4a}$ and R$^{4b}$ are the same or different and each represents R$^4$, or they form morpholino together with the adjacent nitrogen atom), —OR$^4$ or —SR$^4$; R$^4$ represents hydrogen, C$_{1-6}$ alkyl or —W—Z wherein W represents C$_{2-6}$ alkylene and Z represents halogen, —NR$^{5a}$R$^{5b}$ (wherein R$^{5a}$ and R$^{5b}$ are the same or different and each represents R$^5$, or they form morpholino together with the adjacent nitrogen atom, —OR$^5$ or —SR$^5$; R$^5$ represents hydrogen, C$_{1-6}$ alkyl or—W$^a$—Z$^a$ wherein W$^a$ has the same meaning as W mentioned above and Z$^a$ represents halogen, —NR$^{6a}$R$^{6b}$ (wherein R$^{6a}$ and R$^{6b}$ are the same or different and each represents R$^6$, or they form morpholino together with the adjacent nitrogen atom), —OR$^6$ or —SR$^6$; and R$^6$ represents hydrogen or C$_{1-6}$ alkyl; or R$^1$ represents —COY in which Y represents hydrogen, —NR$^{4a}$R$^{4b}$ (wherein R$^{4a}$ and R$^{4b}$ have the same meanings as defined above) or —OR$^4$ (wherein R$^4$ has the same meaning as defined above; R$^2$ represents hydrogen, halogen, nitro, —NR$^{4A}$R$^{4B}$ (wherein R$^{4A}$ and R$^{4B}$ have the same meanings as R$^{4a}$ and R$^{4b}$ mentioned above or they represent optionally halogen-substituted C$_{1-6}$ alkanoyl or —OR$^{4c}$ (wherein R$^{4c}$ has the same meaning as R$^4$ mentioned above); and R$^3$ represents hydrogen, halogen, hydroxyl, C$_{1-6}$ alkoxyl or benzyloxy; or pharmaceutically acceptable salts thereof.

2. The compound according to claim 1, wherein R$^1$ is —CH$_2$NR$^{4a}$R$^{4b}$.

3. The compound according to claim 2, wherein —NR$^{4a}$R$^{4b}$ is selected from the group consisting of —N(CH$_2$CH$_2$OH)$_2$, —N(CH$_2$CH$_2$Cl)$_2$, —NH(CH$_2$)$_2$NH$_2$, —NH(CH$_2$)$_3$NH$_2$, —NH(CH$_2$)$_2$OH, —NH(CH$_2$)$_2$N(CH$_3$)$_2$,

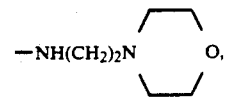

—NH(CH$_2$)$_2$NH(CH$_2$)$_2$OH and —NH(CH$_2$)$_2$O(CH$_2$)$_2$OH.

4. The compound according to any one of claims 1 and 2, wherein R$^2$ is —NR$^{4A}$R$^{4B}$.

5. The compound according to claim 4, wherein —NR$^{4A}$R$^{4B}$ is selected from the group consisting of —NH$_2$, —NH(CH$_2$)$_2$NH$_2$, —NH(CH$_2$)$_3$NH$_2$, —NH(CH$_2$)$_2$N(CH$_3$)$_2$,

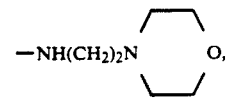

—NH(CH$_2$)$_2$NH(CH$_2$)$_2$NH$_2$ and —NH(CH$_2$)$_2$NH(CH$_2$)$_2$OH.

6. The compound according to any one of claims 1, 2 and 4, wherein R$^3$ is hydroxyl.

7. The compound according to claim 1, which is selected from the group consisting of
5-(2-aminoethyl)amino-2-(2-aminoethyl)aminomethyl-7-hydroxy-6H-pyrazolo[4,5,1-d,e]acridin-6-one,
5-(3-aminopropyl)amino-2-(3-aminopropyl)aminomethyl-7-hydroxy-6H-pyrazolo[4,5,1-d,e]acridin-6-one,
5-(2-dimethylaminoethyl)amino-2-(2-dimethylaminoethyl)aminomethyl-7-hydroxy-6H-pyrazolo[4,5,1-d,e]acridin-6-one,
2-(2-aminoethyl)aminomethyl-7-hydroxy-5-[2-(2-hydroxyethylamino)ethyl]amino-6H-pyrazolo[4,5,1-d,e]acridin-6-one,
5-[2-(2-aminoethylamino)ethyl]amino-2-(2-aminoethyl)aminomethyl-7-hydroxy-6H-pyrazolo[4,5,1-d,e]acridin-6-one,
2-bis(2-hydroxyethyl)aminomethyl-5-(2-dimethylaminoethyl)amino-7-hydroxy-6H-pyrazolo[4,5,1-d,e]acridin-6-one,
7-hydroxy-5-(2-morpholinoethyl)amino-2-(2-morpholinoethyl)aminomethyl-6H-pyrazolo[4,5,1-d,e]acridin-6-one,
5-(2-aminoethyl)amino-7-hydroxy-2-[2-(2-hydroxyethyloxy)ethyl]aminomethyl-6H-pyrazolo[4,5,1-d,e]acridin-6-one,
5-(2-aminoethyl)amino-7-hydroxy-2-(2-hydroxyethyl)aminomethyl-6H-pyrazolo[4,5,1-d,e]acridin-6-one, and
7-hydroxy-5-[2-(2-hydroxyethylamino)ethyl]amino-2-(2-hydroxyethyl)aminomethyl-6H-pyrazolo[4,5,1,-d,e]acridin-6-one.

* * * * *

UNITED STATES PATENT AND TRADEMARK OFFICE
CERTIFICATE OF CORRECTION

PATENT NO. : 5,079,358
DATED : January 7, 1992
INVENTOR(S) : TORU SUGAYA, ET AL.

It is certified that error appears in the above-identified patent and that said Letters Patent is hereby corrected as shown below:

ON THE TITLE PAGE,
IN [54] TITLE

"ANIT-TUMOR" should read --ANTI-TUMOR--.

IN [56] REFERENCES CITED

Under OTHER PUBLICATIONS, "Chem. 677," should read --Chem. 677 (1964),--.

COLUMN 1

Line 3, "ANIT-TUMOR" should read --ANTI-TUMOR--.
Line 46, "gen" should read --gen, halogen,--.
Line 62, "—$NR^{41}R^{4b}$" should read -- —$NR^{4a}R^{4b}$--.

COLUMN 2

Line 28, "carbon 1," should read --carbon atoms such as formyl, acetyl,--.

COLUMN 5

Line 13, "$R^{4a}$," should read --$R^{4a}$, $R^{4b}$--.
Line 54, "R" should read --R'--.

COLUMN 7

Line 13, "(IV)" should read --(VI)--.
Line 20, "alkanoylamino[:" should read --alkanoylamino]:--.

COLUMN 8

Line 51, "(IC)" should read --(Ic)--.

UNITED STATES PATENT AND TRADEMARK OFFICE
CERTIFICATE OF CORRECTION

PATENT NO. : 5,079,358
DATED : January 7, 1992
INVENTOR(S) : TORU SUGAYA, ET AL.

It is certified that error appears in the above-identified patent and that said Letters Patent is hereby corrected as shown below:

COLUMN 10

Line 26, "Process" should read --Synthesis--.

COLUMN 13

TABLE 1-continued, and "NH(CH$_2$)$_2$OH" should read --NH(CH$_2$)$_2$NH(CH$_2$)$_2$OH--.

Line 56, "HeLaS," should read --HeLaS$_3$--.

COLUMN 15

Line 40, "ashed" should read --washed--.
Line 52, "ON" should read --On--.

COLUMN 16

Line 13, insert: --Acute toxicity:-- as subhead.
Line 15, "ddy" should read --ddY--.
Line 17, "LD50" should read --LD$_{50}$--.
Lines 30-33 should read --tumor agents. Specifically, the compounds of the present invention have utility in inhibiting the growth of stomach, lung and leukemia tumor cells.--.

UNITED STATES PATENT AND TRADEMARK OFFICE
CERTIFICATE OF CORRECTION

PATENT NO. : 5,079,358
DATED : January 7, 1992
INVENTOR(S) : TORU SUGAYA, ET AL.

It is certified that error appears in the above-identified patent and that said Letters Patent is hereby corrected as shown below:

COLUMN 18

Line 25, "C, 59.13; H, 5.01; N, 14.47;" should read --C, 59.24; H, 5.39; N, 14.54;--.
Line 32, "cm$^{31\ 1}$:" should read --cm$^{-1}$:--.

COLUMN 19

Line 1, "with mg" should read --with 141 mg--.
Line 36, "dd" should read --dd,--.

COLUMN 21

Line 67, "later" should read --layer--.

COLUMN 25

Line 10, "N, 17.8;" should read --N, 17.18;--.
Line 17, "1652," should read --3420, 1652,--.
Line 51, "N;13 80" should read --N, 13.80--.

COLUMN 27

Line 45, "Compound" should read --Compound 29--.

COLUMN 29

Line 27, "(N-benzyloxycarbonyl-N-ethyl)aminoe-" should read --of 5-[2-(N-benzyloxycarbonyl-N-ethyl)aminoethyl] amino-2-[2-(N-benzyloxycarbonyl-N-ethyl)aminoethyl] aminoethyl-6H-pyrazolo[4,5,1-d,e]acridin-6-one.--.
Line 28 should be deleted.

UNITED STATES PATENT AND TRADEMARK OFFICE
CERTIFICATE OF CORRECTION

PATENT NO. : 5,079,358
DATED : January 7, 1992
INVENTOR(S) : TORU SUGAYA, ET AL.

It is certified that error appears in the above-identified patent and that said Letters Patent is hereby corrected as shown below:

COLUMN 30

Line 41, "75:mg" should read --75 mg--.

COLUMN 31

Line 4, "1514," should read --1514, 1462--.
Line 24, "(KBr" should read --(KBr)--.

COLUMN 32

Line 4, "$cm^{-1}1$:" should read --$cm^{-1}$:--.
Line 8, "ethylamino" (second occurrence) should read --ethyl]amino--.
Line 23, "3.82-3.87)2H," should read --3.82-3.87(2H,--.
Line 42, "FAB-MS(m/z)401$^{+}$+1);" should read --FAB-MS(m/z):401(M$^{+}$+1);--.

COLUMN 33

Line 10, "FAB-MS(m/z)" should read --FAB-MS(m/z):--.
Line 42, "423(M$^{3o}$);" should read --423(M$^{+}$);--.
Line 63, "410(M$^{3o}$+1);" should read --410(M$^{+}$+1);--.

COLUMN 34

Line 27, "$C_{24}H_{31}N_5O_4$32 453" should read --$C_{24}H_{31}N_5O_4$ = 453--.
Line 60, "EXAMPLE 52" should read --EXAMPLE 53--.

UNITED STATES PATENT AND TRADEMARK OFFICE
CERTIFICATE OF CORRECTION

PATENT NO. : 5,079,358
DATED : January 7, 1992
INVENTOR(S) : TORU SUGAYA, ET AL.

It is certified that error appears in the above-identified patent and that said Letters Patent is hereby corrected as shown below:

COLUMN 36

Line 15, "hydroxylthio)" should read --hydroxyethylthio)--.
Line 46, "EI-MS(m/z):" should read --¶ EI-MS(m/z):--.
Line 50, "5Bromo" should read --5-Bromo--.

COLUMN 37

Line 1, "432(M++1);" should read --432($M^+$+1);--.
Line 7, "110 mg)" should read --(110 mg)--.

COLUMN 38

Line 36, "426(M+30 1);" should read --426($M^+$+1);--.

COLUMN 39

Line 11, Close up right margin.
Line 12, Close up left margin.
Line 55, "9.22-9 29" should read --9.22-9.29--.

COLUMN 40

Line 39, "3.23(1H," should read --8.23(1H,--.
Line 48, "mg" should read --36 mg--.
Line 58, "343" should read --342--.

COLUMN 41

Line 37, "6 9 Hz)," should read --6.9 Hz),--.
Line 40, "$C_{18}h_{18}N_4O_2$" should read --$C_{18}H_{18}N_4O_2$--.
Line 57, "32 308" should read --= 308--.

UNITED STATES PATENT AND TRADEMARK OFFICE
CERTIFICATE OF CORRECTION

PATENT NO. : 5,079,358
DATED : January 7, 1992
INVENTOR(S) : TORU SUGAYA, ET AL.

It is certified that error appears in the above-identified patent and that said Letters Patent is hereby corrected as shown below:

COLUMN 42

Line 39, "EI-MS(m/z)" should read --EI-MS(m/z):--.

COLUMN 43

Line 21, "d,e}" should read --d,e]--.
Line 29, "143 mg" should read --140 mg--.

COLUMN 45

Line 64, "above;" should read --above);--.

Signed and Sealed this

Twelfth Day of October, 1993

Attest:

BRUCE LEHMAN

Attesting Officer

Commissioner of Patents and Trademarks